United States Patent
Golonzhka et al.

(10) Patent No.: US 10,858,323 B2
(45) Date of Patent: *Dec. 8, 2020

(54) HDAC INHIBITORS FOR THE TREATMENT OF DIABETIC PERIPHERAL NEUROPATHY

(71) Applicant: REGENACY PHARMACEUTICALS, LLC, Boston, MA (US)

(72) Inventors: Olga Golonzhka, Watertown, MA (US); Matthew B. Jarpe, Quincy, MA (US)

(73) Assignee: REGENACY PHARMACEUTICALS, LLC, Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/026,651

(22) Filed: Jul. 3, 2018

(65) Prior Publication Data

US 2019/0106392 A1    Apr. 11, 2019

Related U.S. Application Data

(63) Continuation of application No. 15/335,971, filed on Oct. 27, 2016, now Pat. No. 10,040,769.

(60) Provisional application No. 62/246,965, filed on Oct. 27, 2015, provisional application No. 62/281,990, filed on Jan. 22, 2016.

(51) Int. Cl.
| | |
|---|---|
| *C07D 239/42* | (2006.01) |
| *A61K 31/505* | (2006.01) |
| *A61K 31/164* | (2006.01) |
| *A61K 31/337* | (2006.01) |
| *A61K 31/495* | (2006.01) |

(52) U.S. Cl.
CPC .......... *C07D 239/42* (2013.01); *A61K 31/164* (2013.01); *A61K 31/337* (2013.01); *A61K 31/495* (2013.01); *A61K 31/505* (2013.01)

(58) Field of Classification Search
None
See application file for complete search history.

(56) References Cited

U.S. PATENT DOCUMENTS

| 10,040,769 B2 | 8/2018 | Golonzhka |
| 2007/0066646 A1 | 3/2007 | Clauzel et al. |
| 2009/0234016 A1 | 9/2009 | Sharma et al. |
| 2011/0300134 A1* | 12/2011 | van Duzer ............ C07C 259/06 424/133.1 |
| 2012/0121502 A1 | 5/2012 | Van Duzer et al. |
| 2012/0190693 A1 | 7/2012 | Van Duzer et al. |
| 2015/0239869 A1 | 8/2015 | Mazitschek et al. |
| 2016/0158231 A1 | 6/2016 | Jarpe et al. |
| 2017/0114023 A1 | 4/2017 | Golonzhka |

FOREIGN PATENT DOCUMENTS

| JP | 2003-095949 | * | 4/2003 |
| JP | 2003-096949 A | | 4/2003 |
| WO | 2001/005392 A2 | | 1/2001 |
| WO | 2011/091213 A2 | | 7/2011 |
| WO | 2012/068109 A2 | | 5/2012 |

OTHER PUBLICATIONS

D'Ydewalle et al. in Nature Medicine 17(8), 968-975 (2011) (Year: 2011).*
U.S. Appl. No. 15/335,971, filed Oct. 27, 2016, Golonzhka.
D'Ydewalle et al. (2011) "HDAC6 inhibitors reverse axonal loss in a mouse model of mutant HSPB1-induced Charcot-Marie-Tooth disease," In Nature Medicine 17(8):968-975.
Freeman et al. (2015) "Metabolic Dysfunction is Restricted to the Sciatic Nerve in Experimental Diabetic Neuropathy," Diabetes. 65(1):228-238.
Matsuyama et al. (2002) "In vivo destabilization of dynamic microtubules by HDAC6-mediated deacetylation," EMBO J. 21(24);6820-6831.
Medori et al. (1985) "Experimental diabetic neuropathy: impairment of slow transport with changes in axon cross-sectional area," In Proceedings of the National Academy of Sciences USA 82:7716-7720.
Kochar et al. (2002) "Sodium valproate in the management of painful neuropathy in type 2 diabetes—a randomized placebo controlled study," Acta Neurologica Scandinavica. 106(5):248-252.
Viader et al. (2013) "Aberrant Schwann Cell Lipid Metabolism Linked to Mitochondrial Deficits Leads to Axon Degeneration and Neuropathy," Neuron. 77(5):886-898.
International Search Report with Written Opinion corresponding to International Patent Application No. PCT/US2016/059075, dated Feb. 17, 2017.

* cited by examiner

*Primary Examiner* — Dennis Heyer
(74) *Attorney, Agent, or Firm* — Brian C. Trinque; Lathrop GPM LLP

(57) ABSTRACT

The invention relates to HDAC inhibitors for use in the treatment of diabetic peripheral neuropathy in a subject in need thereof. Also provided herein are methods for treating diabetic peripheral neuropathy in a subject in need thereof comprising administering to the subject a therapeutically effective amount of an HDAC inhibitor.

4 Claims, 9 Drawing Sheets

1. DMSO
2. 50nM Compound 2
3. 100nM Compound 2
4. 500nM Compound 2
5. 1uM Compound 2
6. 5 uM Compound 2

HDAC INHIBITORS FOR THE TREATMENT OF DIABETIC PERIPHERAL NEUROPATHY

RELATED APPLICATIONS

This application is a continuation of U.S. patent application Ser. No. 15/335,971, filed on Oct. 27, 2016, which application claims priority to U.S. Patent Application No. 62/246,965 filed Oct. 27, 2015, which claims priority to U.S. Patent Application No. 62/281,990, filed Jan. 22, 2016, each of which is incorporated herein by reference in its entirety.

BACKGROUND

Diabetic Peripheral Neuropathy (DPN) is a major complication of diabetes and affects 30-50% of diabetic patients. It is characterized by progressive distal to proximal degeneration of peripheral nerve axons, pain and loss of sensation. The underlying mechanisms of DPN are poorly understood and despite the prevalence and considerable symptom severity, therapeutic intervention options are limited.

Histone deacetylase (HDAC) enzymes represent attractive therapeutic targets in the treatment of diabetic peripheral neuropathy.

SUMMARY

Provided herein are pharmaceutical compounds for use in the treatment of diabetic peripheral neuropathy in a subject in need thereof. Also provided herein are methods for treating diabetic peripheral neuropathy in a subject in need thereof.

DETAILED DESCRIPTION

Figure 1A:
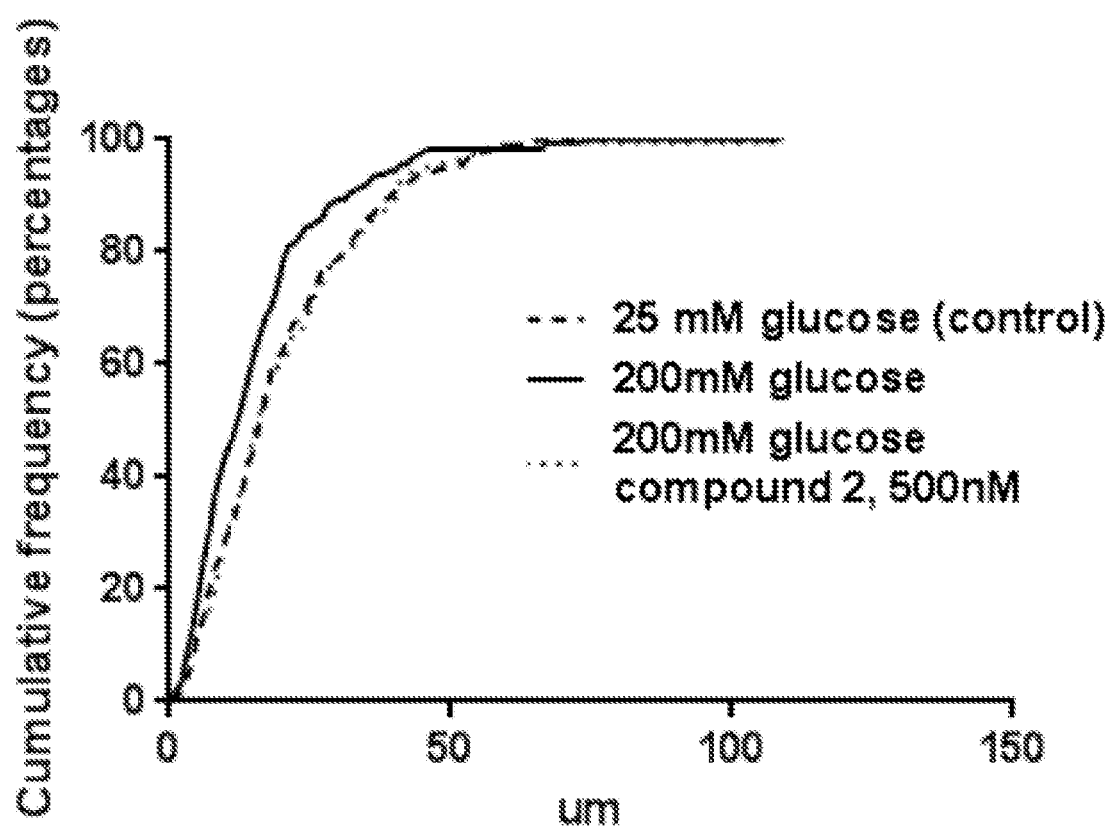
FIG. 1A shows the total distance traveled by a population of mitochondria under each condition (25 mM glucose (control), 200 mM glucose or 200 mM glucose and 500 nM Compound 2) as described in Example 4.

Provided herein are pharmaceutical compounds for use in the treatment of diabetic peripheral neuropathy in a subject in need thereof. Also provided herein are methods for treating diabetic peripheral neuropathy in a subject in need thereof. Specifically, provided herein are HDAC6 inhibitors for the treatment of diabetic peripheral neuropathy.

Thus, in an aspect, provided herein is a method for treating or preventing diabetic peripheral neuropathy in a subject in need thereof comprising administering to the subject a therapeutically effective amount of an HDAC6 inhibitor.

In an embodiment, the HDAC6 inhibitor is an HDAC6-specific inhibitor.

The compounds provided herein (e.g., Compound 1 and Compound 2) are effective at reversing tacticle allodynia in a rat model of diabetic neuropathy (see Example 5). Further, HDAC-6 specific inhibitor, Compound 1, has shown disease modifying effects in the diabetic neuropathy model (Example 5). This result indicates that HDAC6 is a promising target for the treatment of peripheral neuropathies. Further, without being bound by a theory, it is suggested that HDAC6 inhibitors exert their effects at least partially by restoring normal axonal transport in a diabetic neuropathy setting (see, e.g., Example 4).

Definitions

Listed below are definitions of various terms used herein. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six ($C_{1-6}$ alkyl), or one and eight carbon atoms ($C_{1-8}$ alkyl), respectively. Examples of $C_{1-6}$ alkyl moieties include, but are not limited to, methyl, ethyl, propyl, isopropyl, n-butyl, tert-butyl, neopentyl, n-hexyl moieties; and examples of $C_{1-8}$ alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkoxy" refers to an —O-alkyl moiety.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have six carbon atoms. In some embodiments, aryl groups have from six to ten carbon atoms ($C_{6-10}$-aryl). In some embodiments, aryl groups have from six to sixteen carbon atoms ($C_{6-16}$-aryl).

The term "heteroaryl" refers to a mono- or poly-cyclic (e.g., bi-, or tri-cyclic or more) fused or non-fused, moieties or ring system having at least one aromatic ring, having from five to ten ring atoms of which one ring atom is selected from S, O, N and Si; zero, one or two ring atoms are additional heteroatoms independently selected from S, O, N and Si; and the remaining ring atoms are carbon. Heteroaryl includes, but is not limited to pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "halo" refers to a halogen, such as fluorine, chlorine, bromine, and iodine.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6-specific" means that the compound binds to HDAC6 to a substantially greater extent, such as 4×, 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6-specific. On the other hand, a compound that binds to HDAC6 with an $IC_{50}$ of 50 nM and to HDAC1 with an $IC_{50}$ of 60 nM is not HDAC6-specific.

The term "inhibitor" is synonymous with the term antagonist.

The term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

Combinations of substituents and variables envisioned by this invention are only those that result in the formation of stable compounds. The term "stable" refers to compounds which possess stability sufficient to allow manufacture and which maintains the integrity of the compound for a sufficient period of time to be useful for the purposes detailed herein (e.g., therapeutic or prophylactic administration to a subject).

The term "subject" refers to a mammal. A subject therefore refers to, for example, dogs, cats, horses, cows, pigs, guinea pigs, and the like. Preferably the subject is a human. When the subject is a human, the subject may be referred to herein as a patient.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as the diabetic peripheral neuropathy. Within the meaning of the present disclosure, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject, e.g., a mammal or human. The term "prevent," "preventing," or "prevention," as used herein comprises the prevention of at least one symptom associated with or caused by the state, disease or disorder being prevented.

Histone Deacetylase (HDAC) Inhibitors

In an aspect, provided herein is a method for treating or preventing diabetic peripheral neuropathy in a subject in need thereof comprising administering to the subject a therapeutically effective amount of an HDAC6 inhibitor.

In an embodiment, the HDAC6 inhibitor is an HDAC6-specific inhibitor.

In an embodiment, the HDAC6 inhibitor is a compound of Formula Ia:

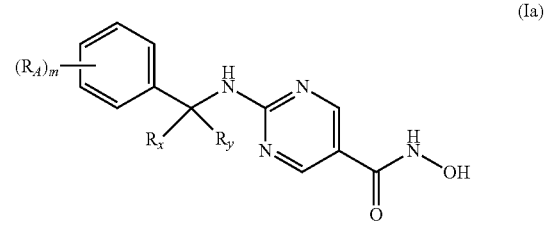

(Ia)

or a pharmaceutically acceptable salt thereof, wherein, $R_x$ is selected from H and $C_{1-6}$-alkyl;

$R_y$ is selected from H and $C_{1-6}$-alkyl;

or $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, or haloalkyl; and m is 0, 1, or 2.

In an embodiment, the compound of Formula Ia is selected from the following:
Compound 1
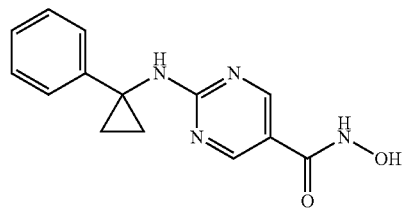
Compound 3
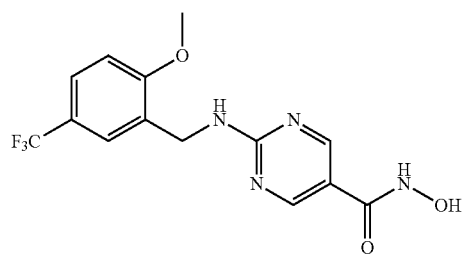
32
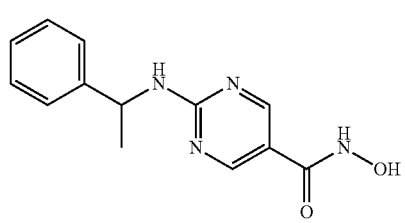
33
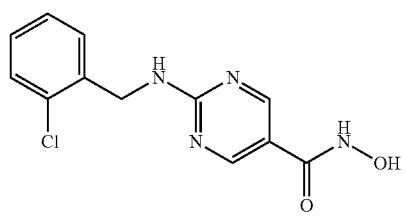
34
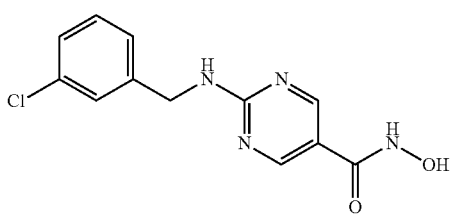
35
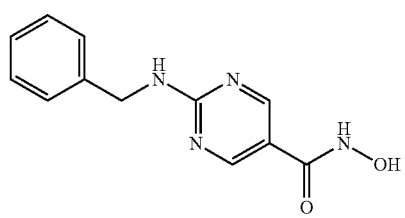
36
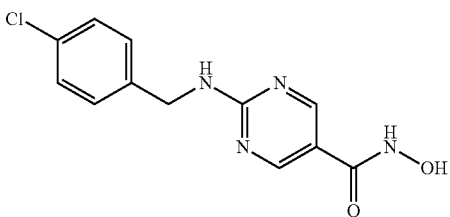
37
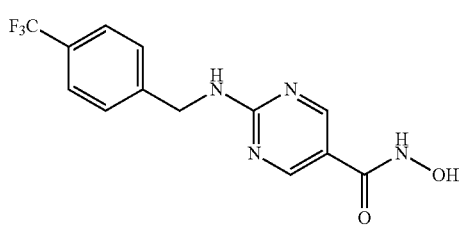
38
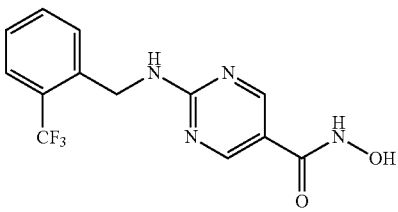
40
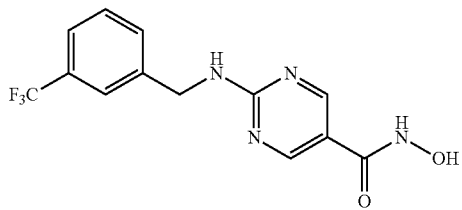
45
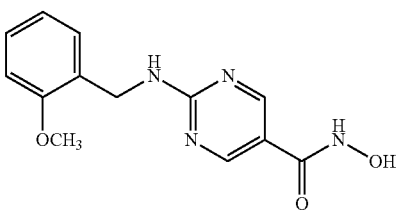
48
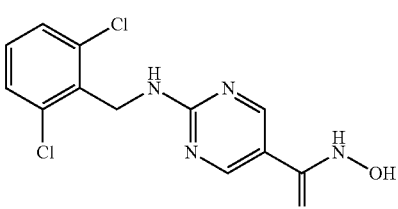
49
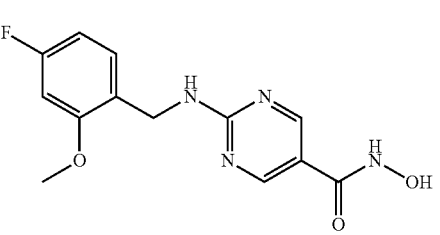

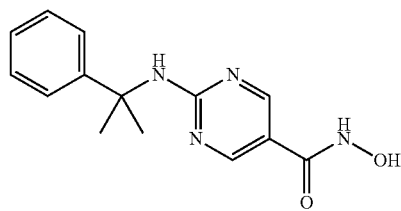
50
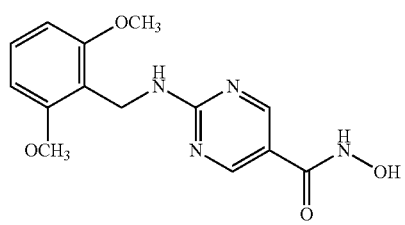
51
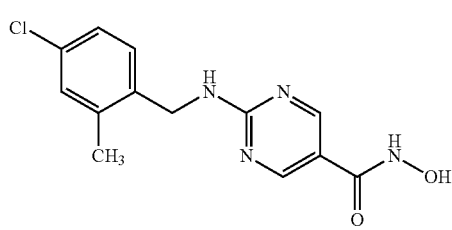
52
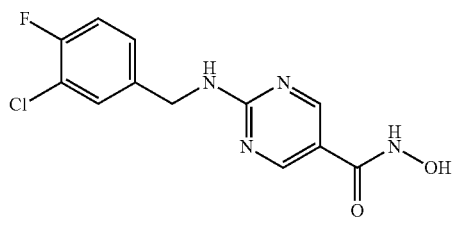
53
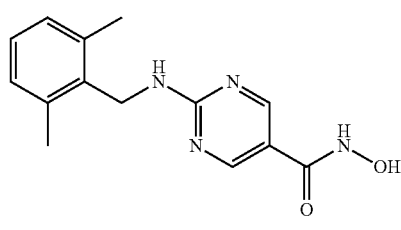
54
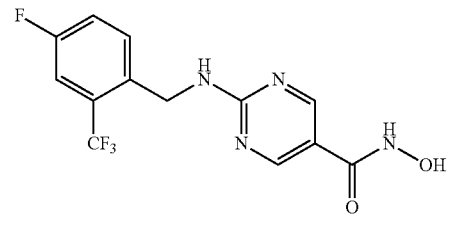
57
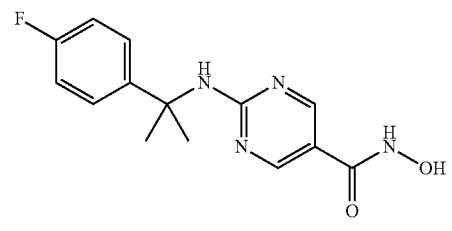
68
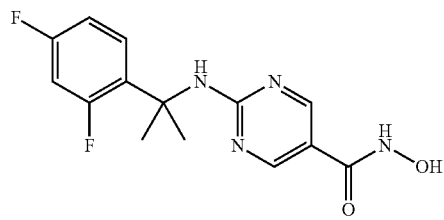
70
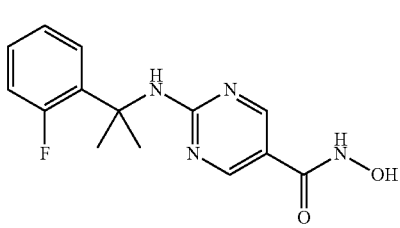
71
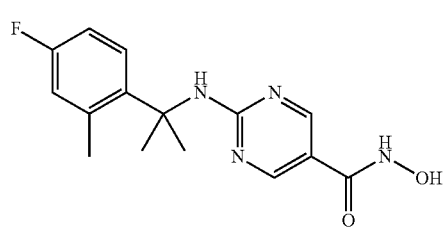
72
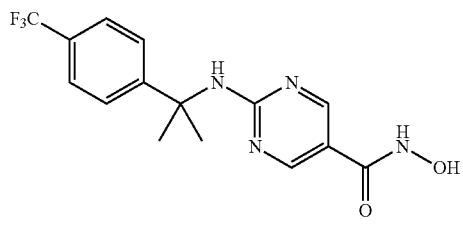
74
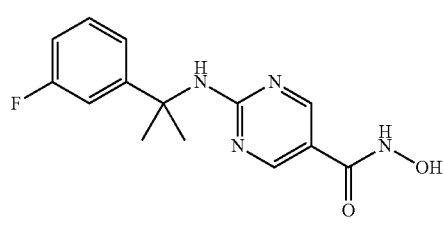
75
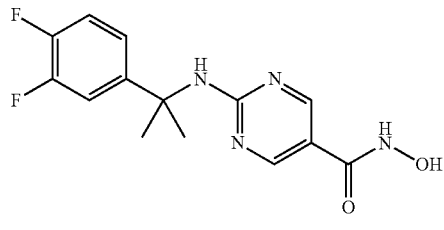
76
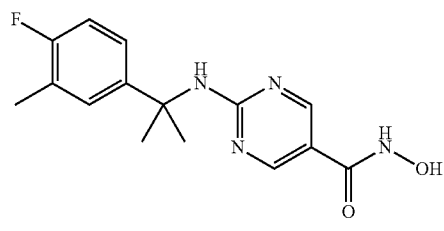
78

-continued
80
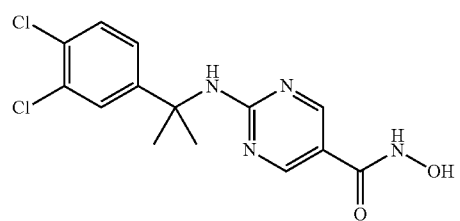
81
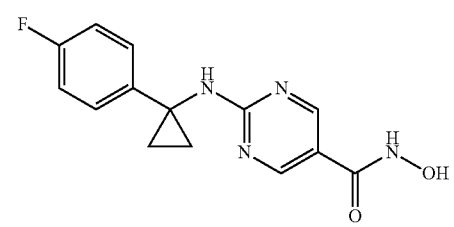
82
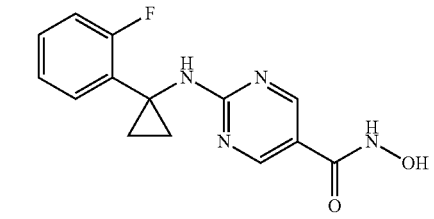
83
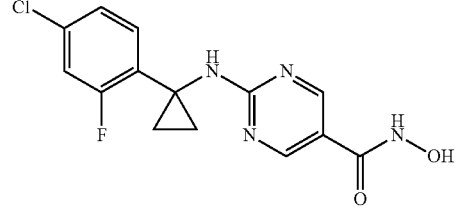
84
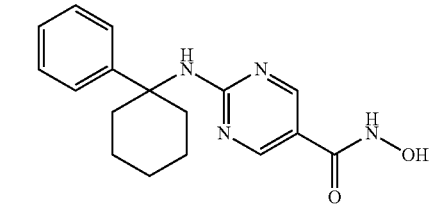
86
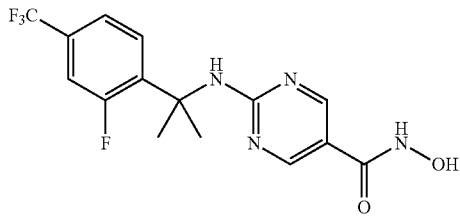
97
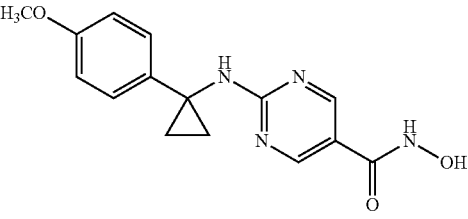
-continued
87
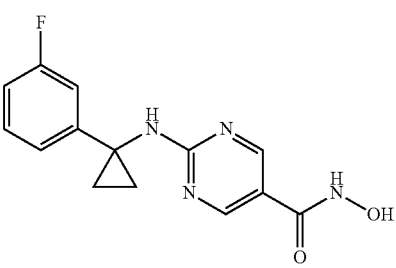
88
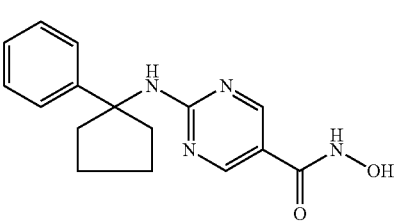
90
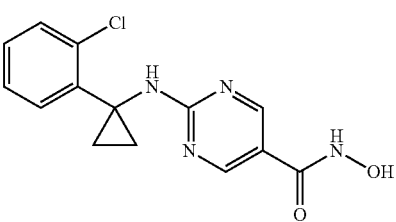
91
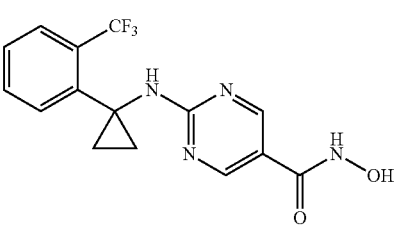
92
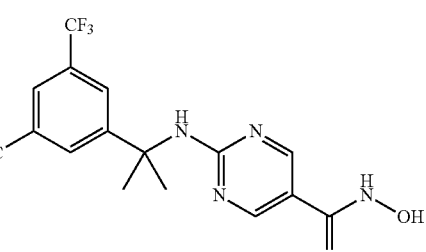
93
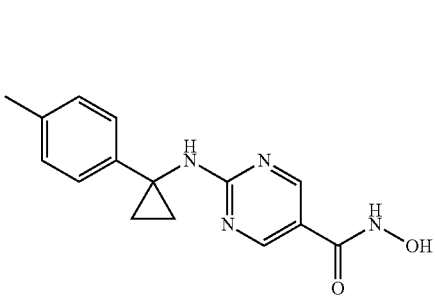

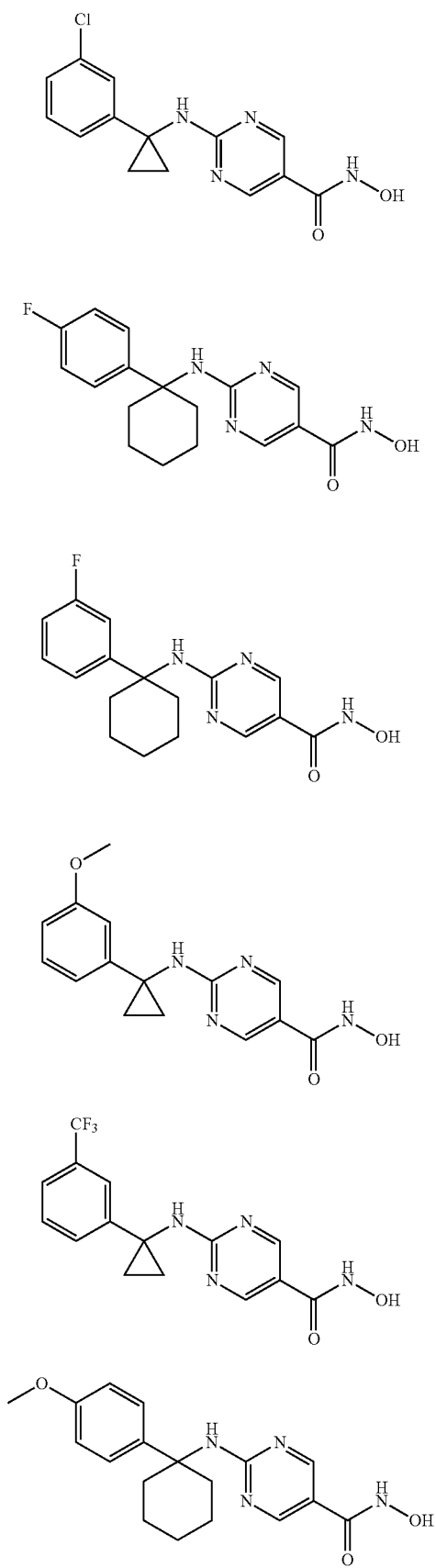

131 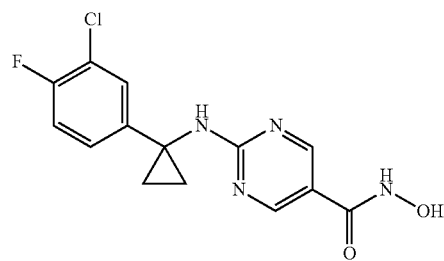
132 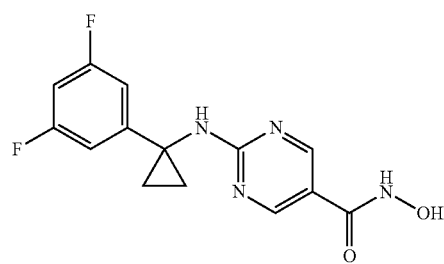
133 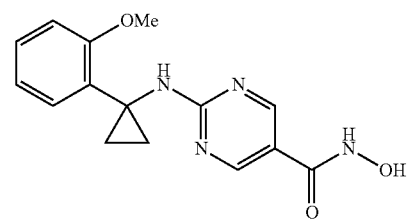
134 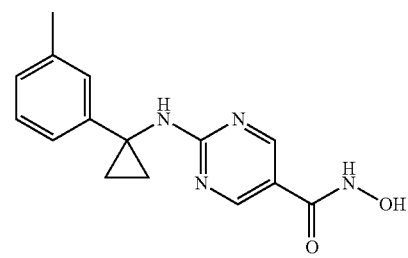
135 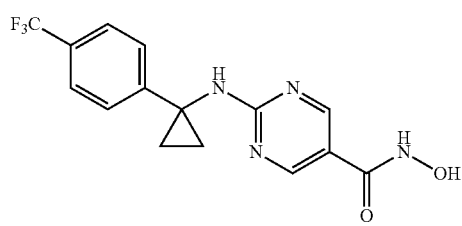
136 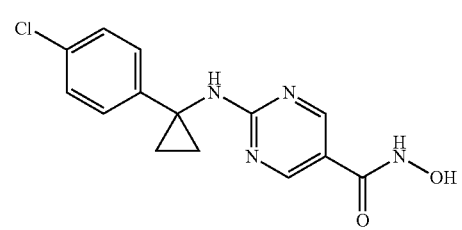
137 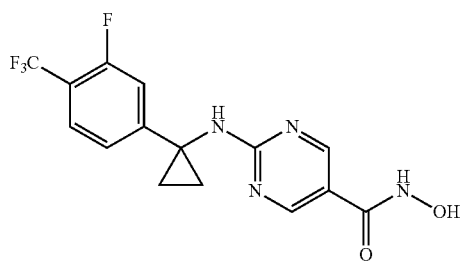
138 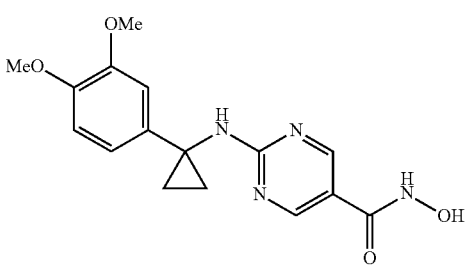
139 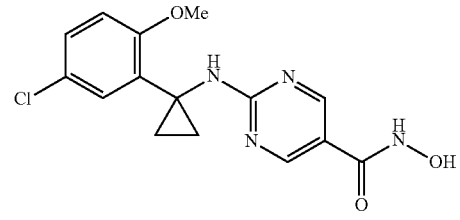
140 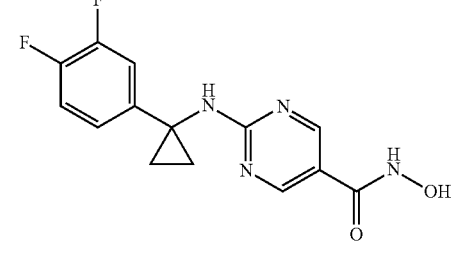
141 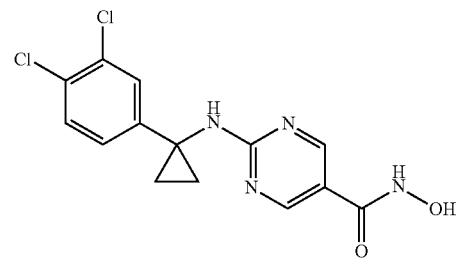
142 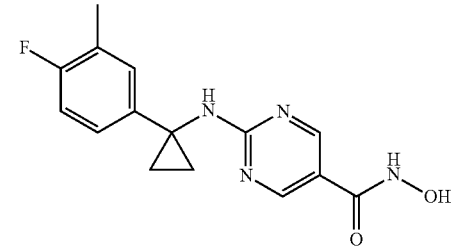

143
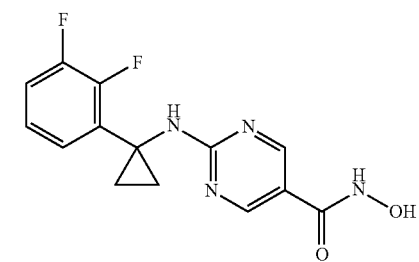
144
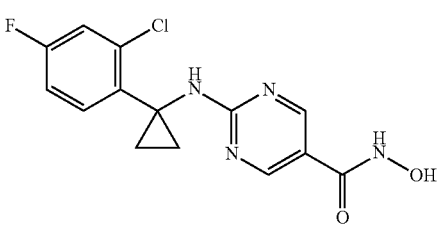
145
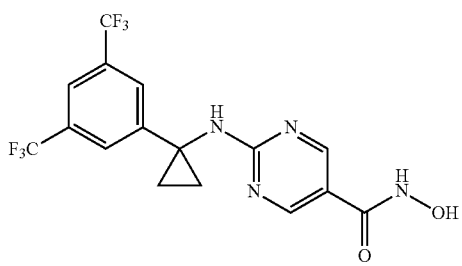
146
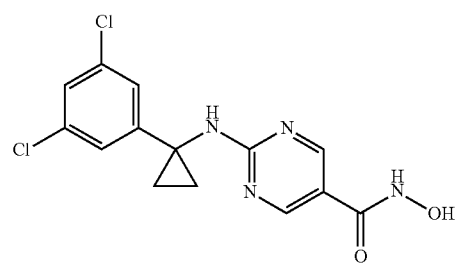
147
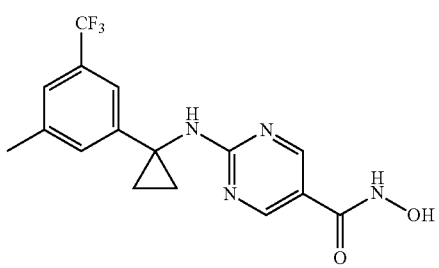
148
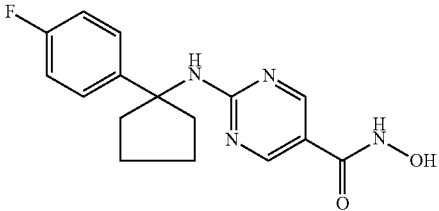
151
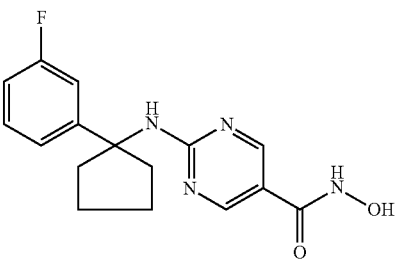
152
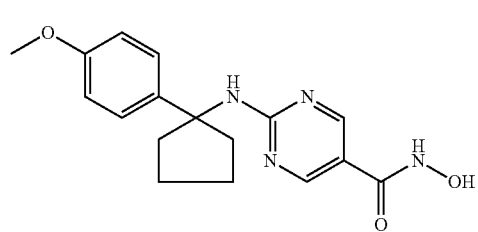
153
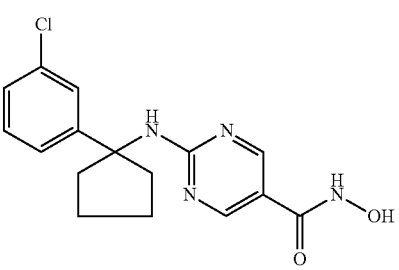
or pharmaceutically acceptable salts thereof.
In an embodiment, the compound of Formula Ia is selected from the following:
Compound 1
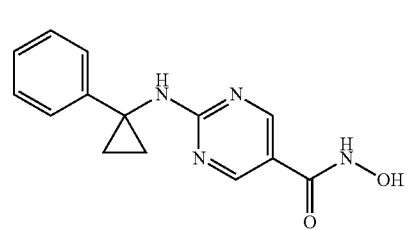
Compound 3
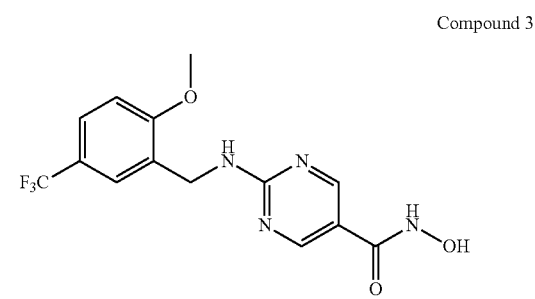

-continued

Compound 101

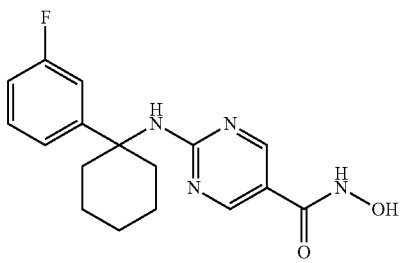

or pharmaceutically acceptable salts thereof.

In an embodiment, the HDAC6 inhibitor provided herein is a compound of Formula I:

(I)

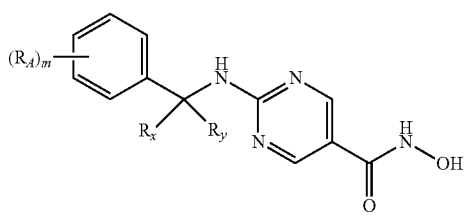

or a pharmaceutically acceptable salt thereof,
wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, or haloalkyl; and m is 0, 1, or 2.

In an embodiment, the compound of Formula I is selected from the following:

Compound 1

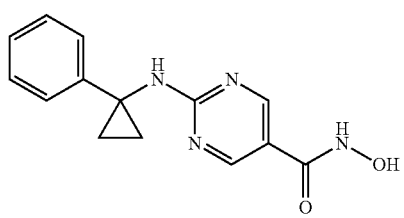

Compound 101

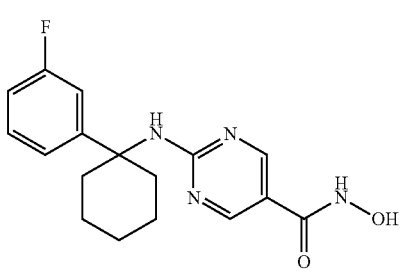 [SMILES: O=C(NO)c1cnc(NC2(c3cccc(F)c3)CCCCC2)nc1]

or pharmaceutically acceptable salts thereof.

Although the compounds of Formulae Ia and I are depicted in their neutral forms, in some embodiments, these compounds are used in a pharmaceutically acceptable salt form.

In a further embodiment, the compound of Formula I is an HDAC6-specific inhibitor, i.e., the compound of Formula I has a selectivity for HDAC6 when tested in an HDAC enzyme assay of about 5 to 1000 fold greater than for other HDACs.

The preparation and properties of certain HDAC6 specific inhibitors according to Formula Ia and I are provided in International Patent Application No. PCT/US2011/060791, the entire content of which is incorporated herein by reference in its entirety.

In another embodiment, the HDAC6 inhibitor provided herein is a compound of Formula II:

(II)

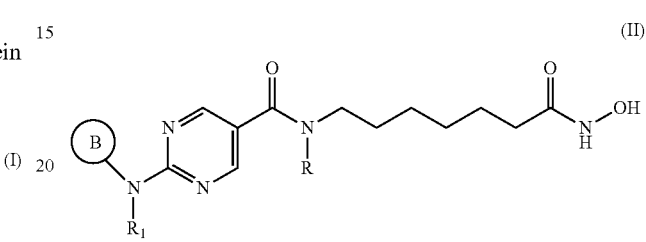

or a pharmaceutically acceptable salt thereof, wherein ring B is aryl or heteroaryl optionally substituted by OH, halo, or $C_{1-6}$-alkyl;

$R_1$ is aryl or heteroaryl optionally substituted by OH, halo, or $C_{1-6}$-alkyl; and R is H or $C_{1-6}$-alkyl.

In an embodiment, the compound of Formula II is selected from the following:

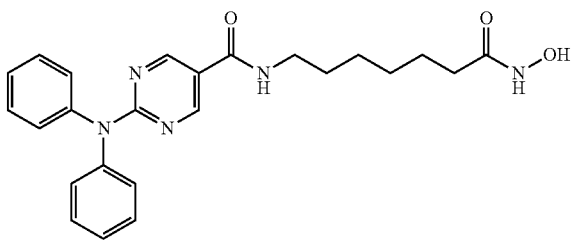

2-(diphenylamino)-N-(7-(hydroxyamino)-7-oxoheptyl)pyrimidine-5-carboxamide (also referred to herin as "Compound 2") $IC_{50}$(nM)
HDAC6 = 10 HDAC3 = 84 HDAC1 = 58 HDAC2 = 64

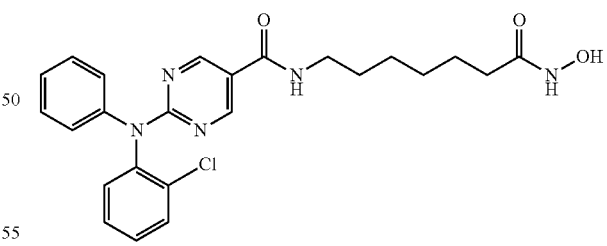

2-((2-chlorophenyl)(phenyl)amino)-N-(7-(hydroxyamino)-7-oxoheptyl)pyrimidine-5-carboxamide $IC_{50}$(nM)
HDAC6 = 4 HDAC3 = 76 HDAC1 = 33 HDAC2 = 54

Although the compounds of Formula II are depicted in their neutral forms, in some embodiments, these compounds are used in a pharmaceutically acceptable salt form.

In a further embodiment, the compound of Formula II is an HDAC6-specific inhibitor, i.e., it has a selectivity for HDAC6 when tested in an HDAC enzyme assay of about 5 to 1000 fold greater than for other HDACs.

The syntheses of compounds of Formula II (e.g., Compound 2) are provided in PCT/US2011/021982; the content of this application is incorporated herein by reference in its entirety.

In an aspect, provided herein is a compound, which is:

or a pharmaceutically acceptable salt thereof.

In some embodiments, the compounds described herein are unsolvated. In other embodiments, one or more of the compounds are in solvated form. As known in the art, the solvate can be any of pharmaceutically acceptable solvent, such as water, ethanol, and the like.

Methods

HDAC6 (Histone Deacetylase 6) inhibitors have shown efficacy in animal models of hematologic cancers and CNS disorders. Provided herein is a use of HDAC6 inhibitors for the treatment or prevention of diabetic peripheral neuropathy.

As used herein, and unless otherwise specified, the term "Diabetic Peripheral Neuropathy" (DPN), also called diabetic neuropathy, DN or "Diabetic Peripheral Neuropathic Pain" (DPNP), refers to chronic pain caused by neuropathy associated with diabetes mellitus. The classic presentation of DPN is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

Compounds 1, 2, and 3 have been studied in models of DPN (see, e.g., Example 5). Compound 2 has been studied in in vitro and in vivo models of DPN (see Examples 4 and 5).

In one aspect, provided herein are methods of treating or preventing a diabetic peripheral neuropathy in a subject in need thereof comprising administering to the subject a therapeutically effective amount of an HDAC6 inhibitor.

In an embodiment of the method, the HDAC6 inhibitor is an HDAC6-specific inhibitor.

In an embodiment of the method, the HDAC6 inhibitor is a compound of Formula Ia, or a pharmaceutically acceptable salt thereof.

In a specific embodiment, the compound of Formula Ia is:

or a pharmaceutically acceptable salt thereof.

In an embodiment of the method, the HDAC6 inhibitor is a compound of Formula I, or a pharmaceutically acceptable salt thereof.

In a specific embodiment, the compound of Formula I is:

or a pharmaceutically acceptable salt thereof.

In a specific embodiment, the compound of Formula I is:

or a pharmaceutically acceptable salt thereof.

In another embodiment, the HDAC6 inhibitor is a compound of Formula II, or a pharmaceutically acceptable salt thereof.

In a specific embodiment, the compound of Formula II is:

or a pharmaceutically acceptable salt thereof.

In another specific embodiment, the compound of Formula II is:

or a pharmaceutically acceptable salt thereof.

For any of the above methods or uses, the required dosage will vary depending on the mode of administration, the particular condition to be treated and the effect desired.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg (including e.g., about 10 mg to 500 mg) of the compound(s) of this invention per day in single or multiple doses. Thus, in an embodiment of the methods of treatment provided herein, the compound according to the present invention is administered at a dosage of 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg per day. In a further embodiment, the compound according to the present invention is administered at a dosage of 20 mg, 40 mg, 60 mg, 80 mg, 100 mg, 120 mg, 140 mg, 160 mg, 180 mg, or 200 mg per day. In yet another embodiment, the compound according to the present invention is administered at a dosage of 80 or 120 mg per day. In an embodiment, the compound according to the present invention is administered one time daily. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Use

Also provided herein is an HDAC6 inhibitor for use in the treatment or prevention of diabetic peripheral neuropathy in a subject. In an embodiment, the HDAC6 inhibitor is an HDAC6-specific inhibitor.

In a further embodiment, HDAC6 inhibitor is a compound of Formula Ia, or a pharmaceutically acceptable salt thereof. In yet a further embodiment, the HDAC inhibitor is a compound of Formula I, or a pharmaceutically acceptable salt thereof. The compound of Formulae Ia or I can be selected from the group consisting of:

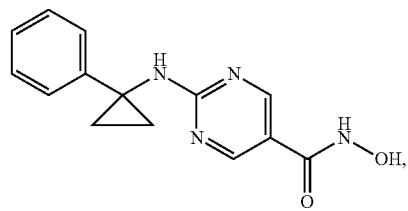

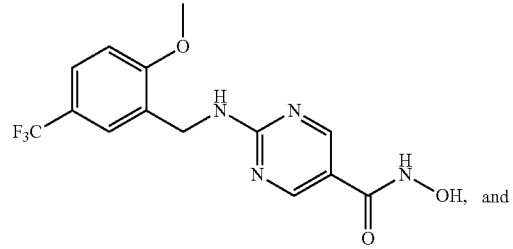

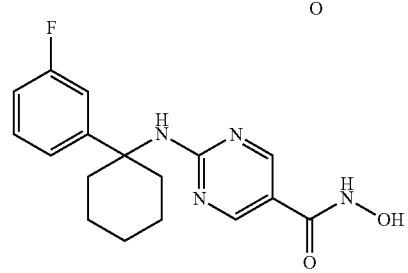

or pharmaceutically acceptable salt thereof.

In another embodiment, the HDAC6 inhibitor is a compound of Formula II, or a pharmaceutically acceptable salt thereof.

In an embodiment, the compound of Formula II is:

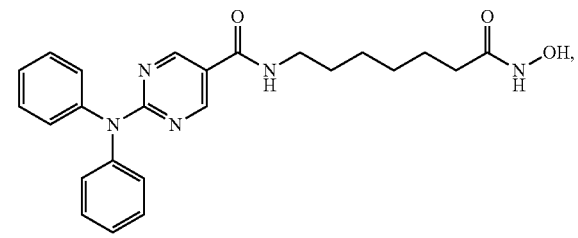 [SMILES: O=C(CCCCCCNC(=O)c1cnc(N(c2ccccc2)c2ccccc2)nc1)NO]

or a pharmaceutically acceptable salt thereof.

In another embodiment, the compound of Formula II is:

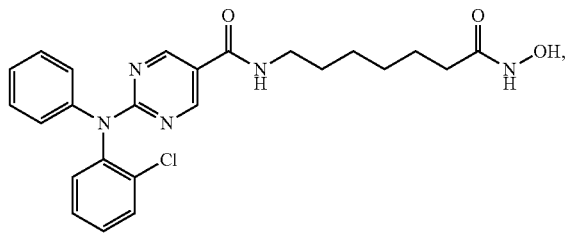 [SMILES: O=C(CCCCCCNC(=O)c1cnc(N(c2ccccc2)c2ccccc2Cl)nc1)NO]

or a pharmaceutically acceptable salt thereof.

In an aspect, provided herein is a use of a compound selected from the group consisting of:

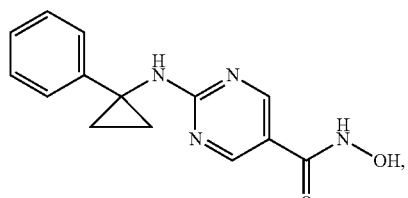

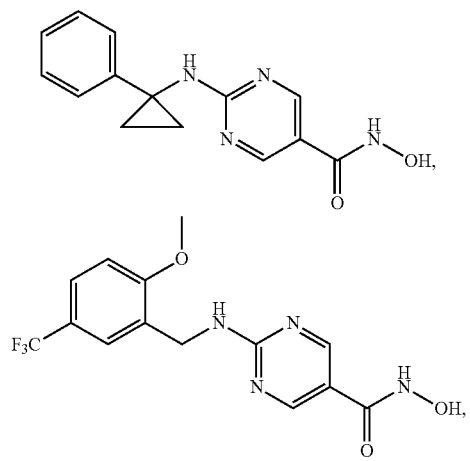

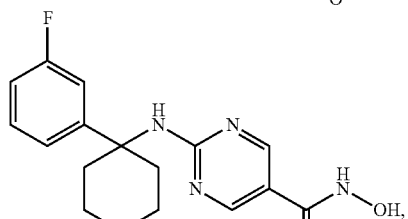

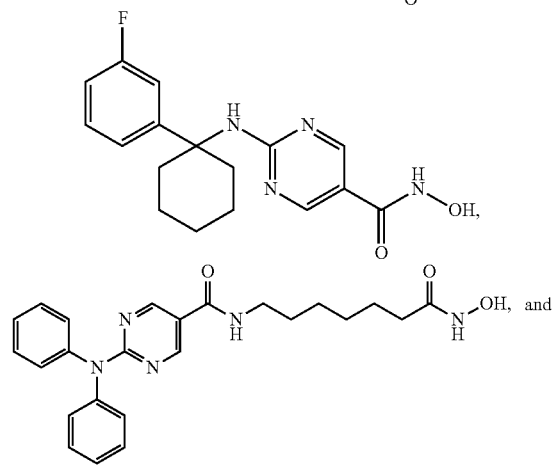

or pharmaceutically acceptable salts thereof, for the preparation of a medicament for the treatment or prevention of diabetic peripheral neuropathy.

In an embodiment of this use, the compound is

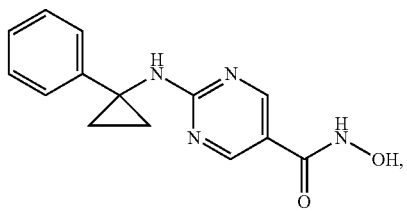 [SMILES: O=C(NO)c1cnc(NC2(c3ccccc3)CC2)nc1]

or a pharmaceutically acceptable salt thereof.

In another embodiment of this use, the compound is

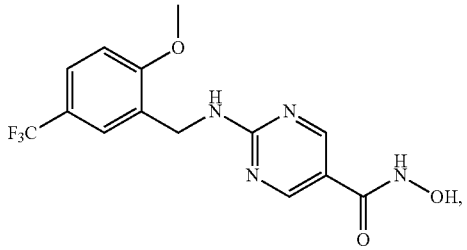 [SMILES: COc1ccc(C(F)(F)F)cc1CNc1ncc(C(=O)NO)cn1]

or a pharmaceutically acceptable salt thereof.

In another embodiment of this use, the compound is

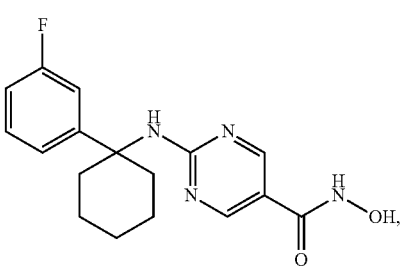 [SMILES: O=C(NO)c1cnc(NC2(c3cccc(F)c3)CCCCC2)nc1]

or a pharmaceutically acceptable salt thereof.

In another embodiment of this use, the compound is

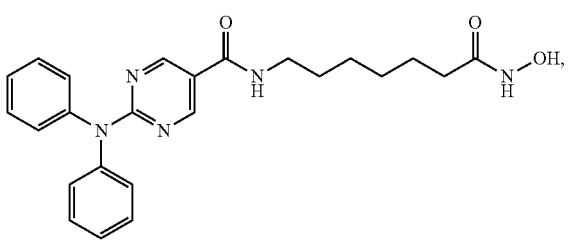 [SMILES: O=C(CCCCCCNC(=O)c1cnc(N(c2ccccc2)c2ccccc2)nc1)NO]

or a pharmaceutically acceptable salt thereof.

In another embodiment of this use, the compound is

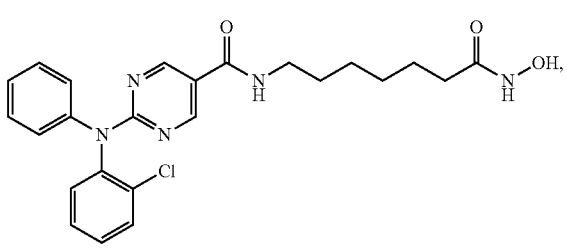 [SMILES: O=C(CCCCCCNC(=O)c1cnc(N(c2ccccc2)c2ccccc2Cl)nc1)NO]

or a pharmaceutically acceptable salt thereof.

Pharmaceutical Compositions

In another aspect, the invention provides a pharmaceutical composition comprising any of the compounds provided herein, or pharmaceutically acceptable salts thereof, together with a pharmaceutically acceptable carrier for use in the treatment or prevention of diabetic peripheral neuropathy.

The pharmaceutical compositions of the present invention comprise a therapeutically effective amount of a compound of the present invention formulated together with one or more pharmaceutically acceptable carriers. The term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Compounds of the invention can be administered as pharmaceutical compositions by any conventional route, in particular enterally, for example, orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substitutents, derivatives, formulations and/or methods of the invention may be made without departing from the spirit of the invention and the scope of the appended claims.

Example 1: Synthesis of Compounds of Formulae Ia and I

A. Synthesis of N-hydroxy-2-((1-phenylcyclopropyl)amino)pyrimidine-5-carboxamide (Compound 1)

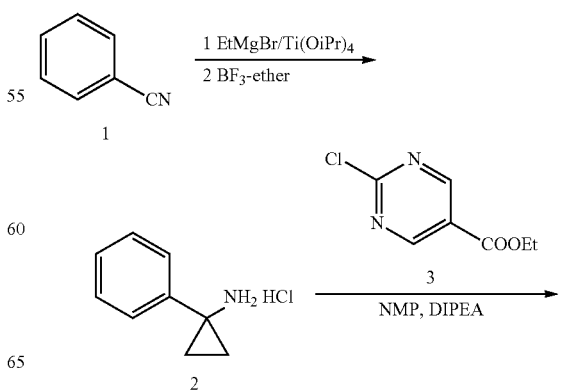

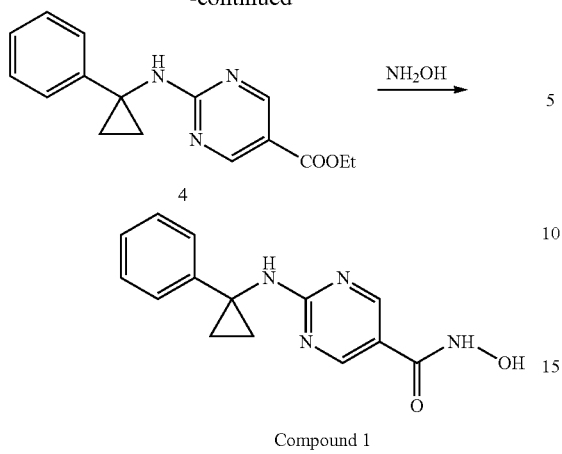

Compound 1

Synthesis of Intermediate 2

A solution of intermediate 1, benzonitrile, (250 g, 1.0 equiv.), and Ti(OiPr)$_4$ (1330 ml, 1.5 equiv.) in MBTE (3750 ml) was cooled to about −10 to −5° C. under a nitrogen atmosphere. EtMgBr (1610 ml, 3.0 M, 2.3 equiv.) was added dropwise over a period of 60 min., during which the inner temperature of the reaction was kept below 5° C. The reaction mixture was allowed to warm to 15-20° C. for 1 hr. BF$_3$-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3 L×2) and EtOAc (3 L×2), and the combined organic layers were dried with anhydrous Na$_2$SO$_4$ and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of intermediate 2.

Synthesis of Intermediate 4

Intermediate 2 (620 g, 1.0 equiv) and DIPEA (1080 g, 2.2 equiv. were dissolved in NMP (3100 ml) and stirred for 20 min. Intermediate 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of intermediate 4 (solid, 86.8%).

Synthesis of N-hydroxy-2-((1-phenylcyclopropyl)amino)pyrimidine-5-carboxamide (Compound 1)

A solution of MeOH (1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hour, and was filtered to remove the solid. Intermediate 4 (450 g, 1.0 equiv.) was added to the reaction mixture in one portion, and stirred at 10° C. for two hours until intermediate 4 was consumed. The reaction mixture was adjusted to a pH of about 8.5-9 through addition of HCl (6N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

B. Synthesis of N-hydroxy-2-((2-methoxy-5-(trifluoromethyl)benzyl)amino)pyrimidine-5-carboxamide (Compound 3)

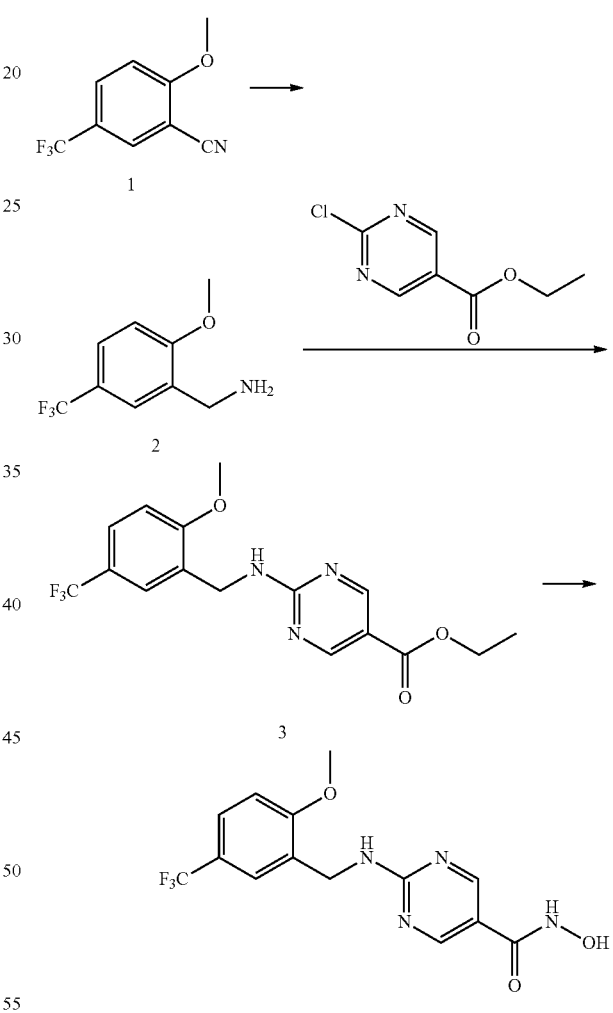

Compound 3

Synthesis of Intermediate 2

To mixture of 2-methoxy-5-(trifluoromethyl)benzonitrile (300 mg, 1.5 mmol) in Dry THF (15 ml) was added LiAlH$_4$ (285 mg, 7.5 mmol, solid) slowly at ice temperature. Then the mixture was stirred at room temperature overnight. After the reaction was deemed complete from TLC, the mixture was quenched with sat. NH$_4$Cl and extracted with EA (1*20 ml). The organic layer was dried and concentrated to afford the crude amine intermediate 2 (300 mg, crude) as light yellow oil.

Synthesis of Intermediate 3

To a solution of crude (2-methoxy-5-(trifluoromethyl) phenyl)-methanamine (300 mg) in NMP (8 ml) was added 2-Cl-pyrimidine (272 mg, 1.0 eq) and DIPEA (943 mg, 5.0 eq). The mixture was stirred at 115° C. for 2 h. The mixture was diluted with water (10 ml), extracted with EA (1*15 ml), dried and concentrated to afford a residue, which was purified by prep-TLC with PE/EA=3:1 to afford intermediate 3 (200 mg, 37.6%, 2 steps) as light yellow solid.

Synthesis of N-hydroxy-2-((2-methoxy-5-(trifluoromethyl)benzyl)amino)pyrimidine-5-carboxamide (Compound 3)

To a mixture of ethyl 2-(2-methoxy-5-(trifluoromethyl) benzylamino)pyrimidine-5-carboxylate (100 mg, 0.28 mmol) in MeOH/DCM (6/2 ml) was added NH$_2$OH (0.5 ml), followed NaOH solution (sat. in MeOH, 1 ml) dropwise at 0° C. The mixture was stirred at 0° C. for 3 hrs. After the reaction was deemed complete from TLC, the mixture was concentrated to remove MeOH and DCM, acidified to pH near 6-7, and then purified by Prep-HPLC to afford the desired product, Compound 3, as white solid (30 mg, 31%). LCMS: m/z=343 (M+H)$^+$. $^1$H NMR (400 MHz, DMSO) δ 11.03 (s, 1H), 8.99 (s, 1H), 8.61 (d, J=17.4 Hz, 2H), 8.22 (t, J=6.2 Hz, 1H), 7.61 (d, J=8.5 Hz, 1H), 7.42 (d, J=1.8 Hz, 1H), 7.19 (d, J=8.6 Hz, 1H), 4.55 (d, J=6.1 Hz, 2H), 3.91 (s, 3H).

Example 2: Synthesis of 2-(diphenylamino)-N-(7-(hydroxyamino)-7-oxoheptyl)pyrimidine-5-carboxamide (Compound 2)

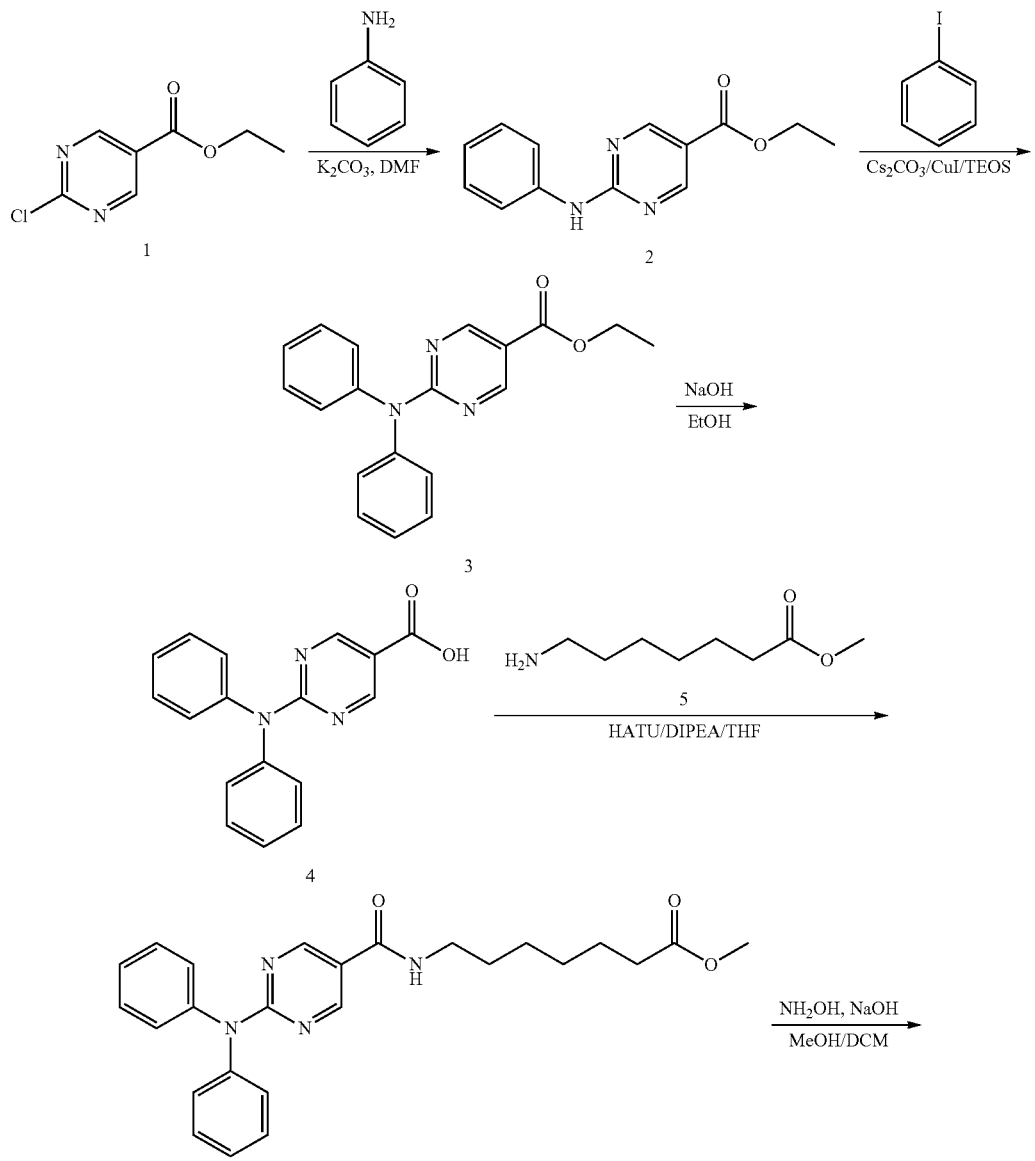

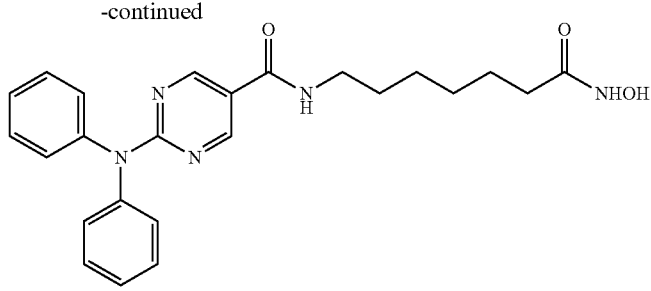

Step 1: Synthesis of Intermediate 2

A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Step 2: Synthesis of Intermediate 3

A mixture of intermediate 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 h. After cooling to r.t., the residue was diluted with EtOAc (200 ml) and 95% EtOH (200 ml), $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

Step 3: Synthesis of Intermediate 4

2N NaOH (200 ml) was added to a solution of intermediate 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Step 4: Synthesis of Intermediate 6

A mixture of intermediate 4 (2.5 g, 8.58 mmol), aminoheptanoate 5 (2.52 g, 12.87 mmol), HATU (3.91 g, 10.30 mmol), DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Step 5: Synthesis of 2-(diphenylamino)-N-(7-(hydroxyamino)-7-oxoheptyl)pyrimidine-5-carboxamide (Compound 2)

A mixture of intermediate 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 3: HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 µM TCEP) to 6 fold their final concentration. The HDAC enzymes (purchased from BPS Biosciences) were diluted to 1.5 fold their final concentration in assay buffer. The tripeptide substrate and trypsin at 0.05 µM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 µM (HDAC1), 10 µM (HDAC2), 17 µM (HDAC3) and 14 µM (HDAC6). Five 1 of compound and 20 µl of enzyme were added to wells of a black, opaque 384 well plate in duplicate. Enzyme and compound were incubated together at room temperature for 10 minutes. Five µl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit. The $IC_{50}$ values for Compounds 1, 2, and 3 are shown below in Table 1.

TABLE 1

| Compound | HDAC1 IC50 (nM) | HDAC2 IC50 (nM) | HDAC3 IC50 (nM) | HDAC6 IC50 (nM) |
|---|---|---|---|---|
| Compound 1 | 94 | 128 | 158 | 1.7 |
| Compound 2 | 58 | 64 | 84 | 10 |
| Compound 3 | 68 | 82 | 105 | 2 |

Example 4: HDAC6 Inhibition Restores Axonal Transport Impaired by High Glucose (Hyperglycemia) in Cultured Neurons Microtubule-based axonal transport plays a pivotal role in normal neuronal function. Deficits in axonal transport have been reported in STZ rats and axonal transport abnormalities are thought to contribute to peripheral nerve dysfunction and degeneration. HDAC6 is a tubulin deacetylase and HDAC6 inhibition has been shown to restore normal axonal transport in different models of neurodegenerative disorders and peripheral neuropathies.

To investigate the effects of hyperglycemia on axonal transport live imaging was used to measure mitochondrial transport in primary rat dorsal root ganglion cells. Primary rat dorsal root ganglion (DRG) neurons (Lonza) were cultured for 5-7 days according to the vendor's protocol. The day before the imaging session cells were infected using CellLight Mitochondria-GFP (BacMam 2.0-based reagent, ThermoFisher Scientific) to fluorescently label mitochondria. Additionally, the media was replaced with media containing 200 mM glucose or 200 mM glucose and 500 nM Compound 2. Media in control wells was replaced with fresh media containing 25 mM glucose (control). Cells were allowed to incubate under these conditions for 24 h. For live imaging cells were maintained in CO2-independent media, containing either 25 mM glucose, 200 mM glucose or 200 mM glucose and 500 mM Compound 2. Imaging was performed using Zeiss 3i system (Intelligent Imaging Innovations) in temperate controlled environment (37 C). Mitochondria were visualized using FITC filter. Time lapse images were acquired every 2 seconds over the course of 2 min and analyzed using Fiji (ImageJ). MtrackJ plugin was used to manually track mitochondrial movements and calculate parameters such as total distance traveled by each mitochondria. Total distance traveled by a population of mitochondria in each condition was plotted as a cumulative frequency plot. Data presented is a pool of 5 independent experiments.

Figure 1B:
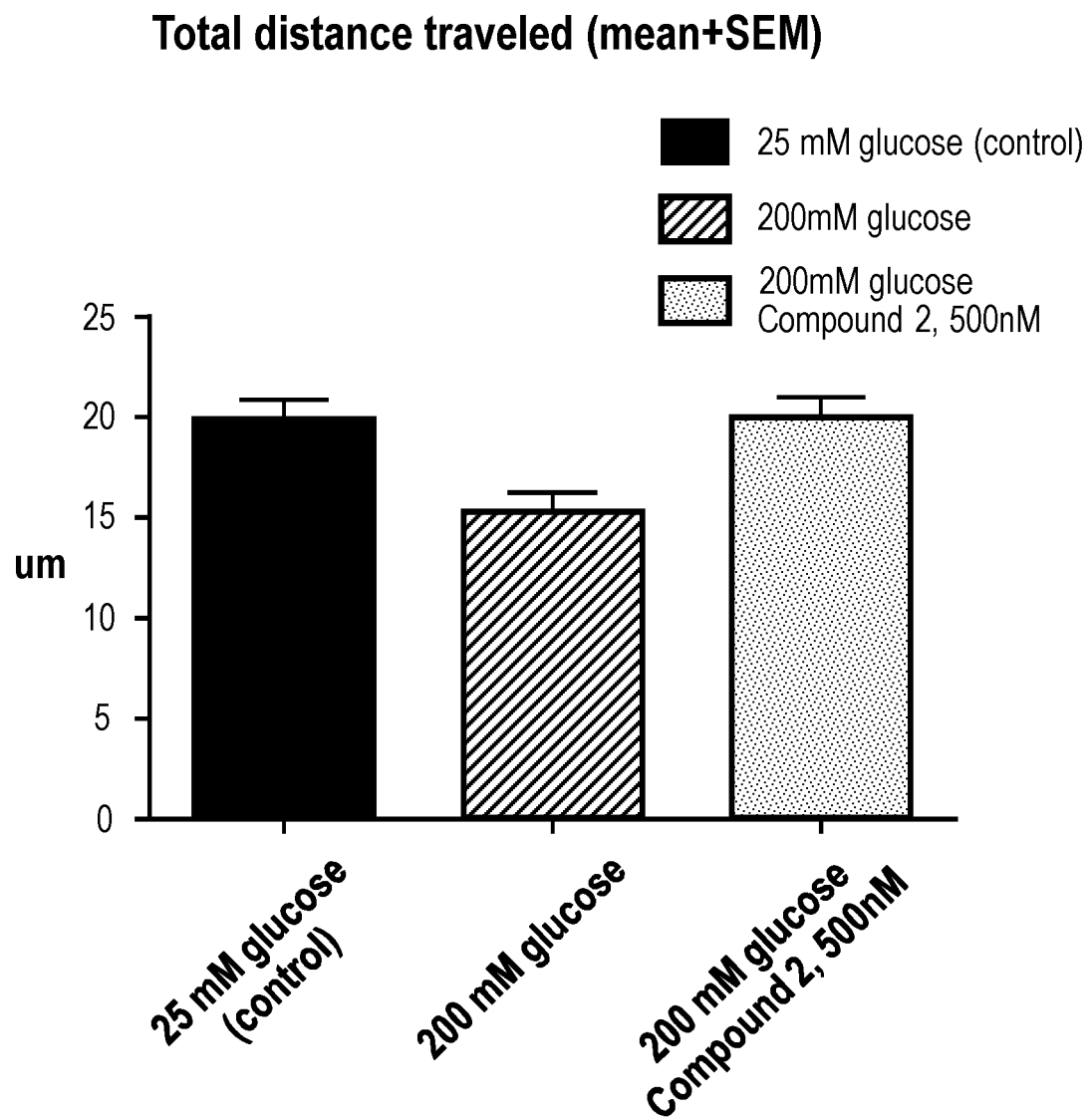
FIG. 1B shows that treatment with Compound 2 restores normal pattern of mitochondrial movement as described in Example 4.

Neurons exposed to high glucose exhibit mitochondrial transport deficits as shown by the shift in the cumulative frequency plot (FIG. 1A) and a decrease in the mean value of the total distance traveled (FIG. 1B). Treatment with Compound 2 restores normal pattern of mitochondrial movement.

This study shows that neurons exposed to high glucose exhibit axonal transport deficits and that treatment with Compound 2 rescues these deficits (see FIG. 1A). Thus, Compound 2 can be used as an effective treatment option for diabetic peripheral neuropathy.

Example 5: HDAC6 Inhibition Reverses Neuropathic Pain in STZ Diabetic Rats

Compounds 1, 2, and 3 were tested for the ability to reverse neuropathy in streptozotocin-induced diabetic rats (STZ rats), a commonly used model of painful DPN. Both compounds reversed tactile allodynia in STZ rats in a dose-dependent manner and restored the pain threshold in these rats to nearly normal levels. In the case of Compound 1, e.g., the positive effect of the drug on pain threshold persisted even after the drug treatment was stopped, suggesting a disease modifying effect of HDAC6 inhibitors in DPN.

Further, Compound 1 penetrates the blood brain barrier, while Compound 2 does not penetrate the blood brain barrier very well.

Diabetes was induced in male SD rats by IV dosing of STZ (60 mg/kg) on study days 0-10. Blood glucose level (BGL) of above 300 mg/dl was observed on study day 3, following STZ dosing, which maintained throughout the study period. On study day 10, the sensitivity of all animals to von Frey filaments was tested and animals that showed a decrease in withdrawal force threshold (average pain threshold of <43 g for both hind paws) were included in the study and assigned to the treatment groups.

Figure 2A:
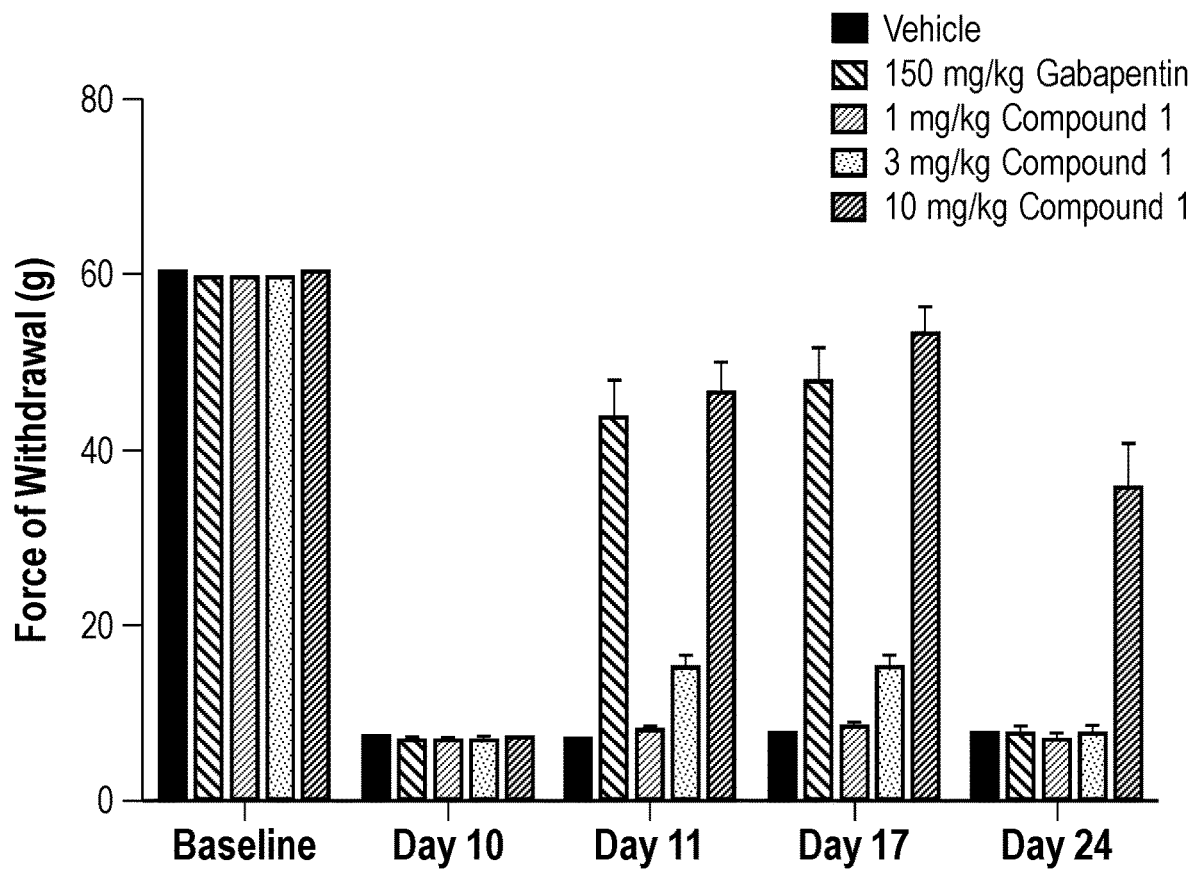
FIG. 2A shows the mean response to Von Frey test (g) in the study of diabetic peripheral neuropathy in STZ diabetic rats upon treatment with Compound 1 as described in Example 5.
Figure 2B:
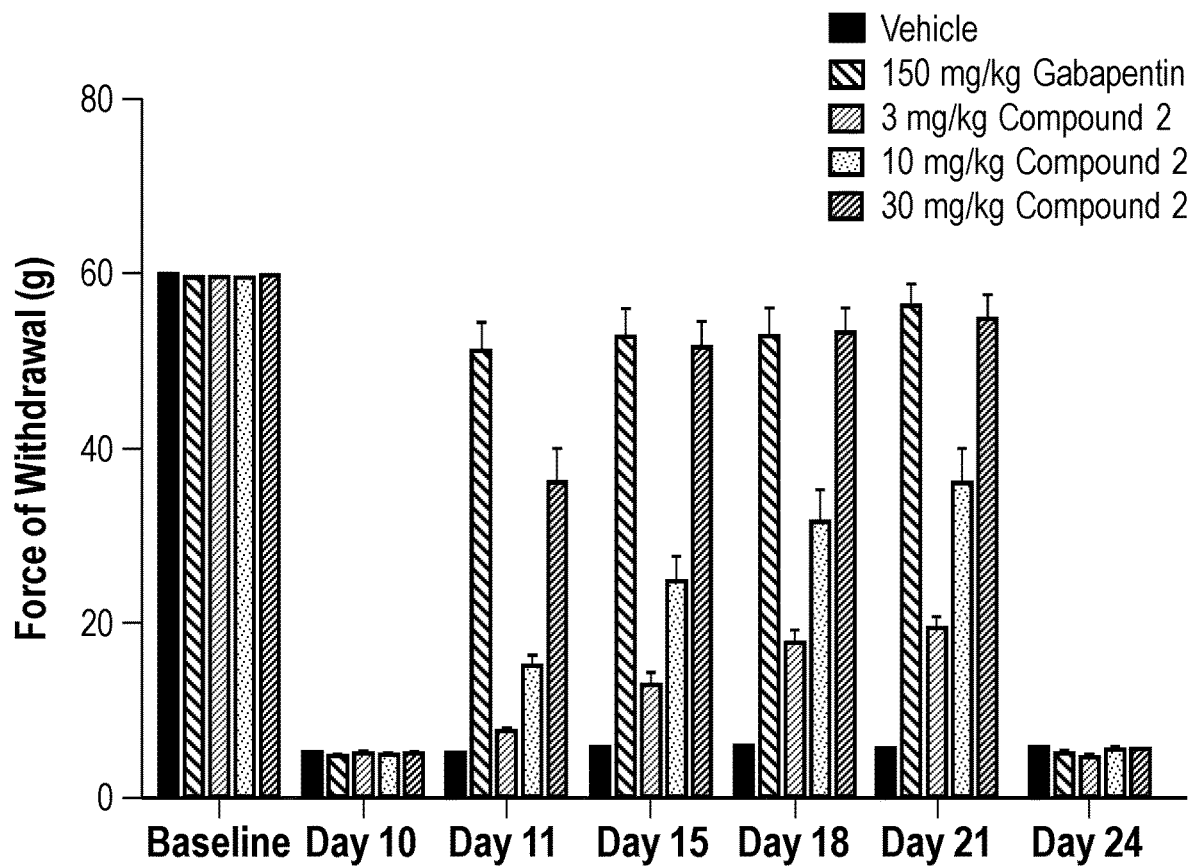
FIG. 2B shows the mean response to Von Frey test (g) in the study of diabetic peripheral neuropathy in STZ diabetic rats upon treatment with Compound 2 as described in Example 5.
Figure 2C:
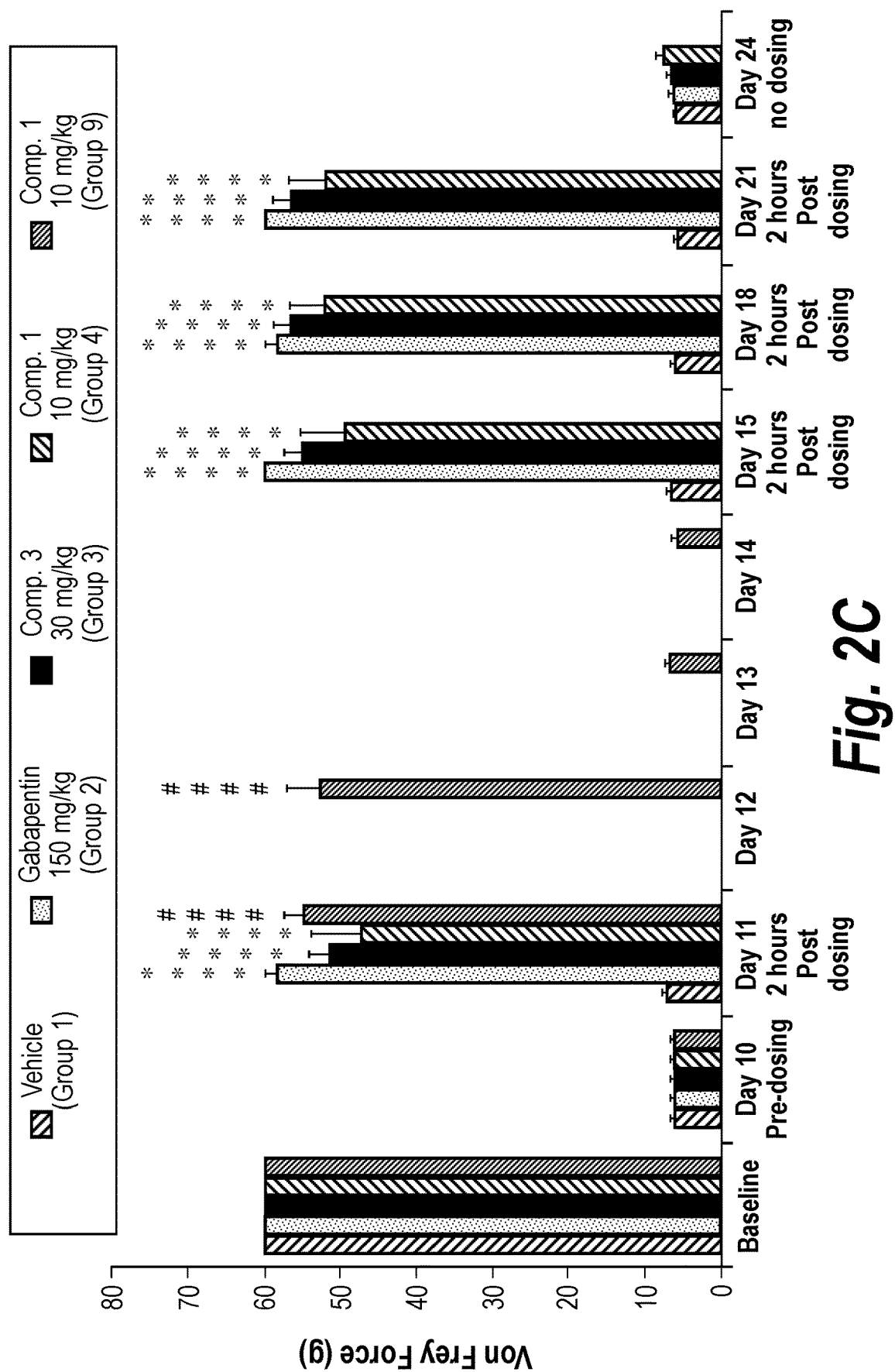
FIG. 2C shows the mean response to Von Frey test (g) in the study of diabetic peripheral neuropathy in STZ diabetic rats upon treatment with Compound 3 as described in Example 5.

Animals were dosed as indicated twice daily for 8 days (e.g., Compound 2 orally at 3, 10, and 30 mg/kg twice daily (BID) on days 11-21 and Compound 1 orally at 1, 3, and 10 mg/kg once daily (QD) on days 11-21). Gabapentin (150 mg/kg) was used as a positive control. Tactile allodynia was measured on the indicated days during dosing and once on day 24, three days after dosing was stopped. The results of the von Frey test upon dosing with Compound 1 are shown in FIG. 2A. The results of the von Frey test upon dosing with Compound 2 are shown in FIG. 2B. The results of the von Frey test upon dosing with Compound 3 are shown in FIG. 2C. Vehicle treated animals experienced low mechanical threshold throughout the treatment period (days 11-21) and also 3 days after the last dose (day 24). Compounds 1, 2, and 3 reversed tactile allodynia in STZ rats in a dose dependent manner and restored the pain threshold in these rats to almost normal levels (see FIGS. 2A, 2B, and 2C). Further, the effect of Compound 1 persisted even after the drug was withdrawn (FIG. 2A, day 24).

Example 6: Compound 2 Increases Tubulin Acetylation in Neurons

Figure 3A:
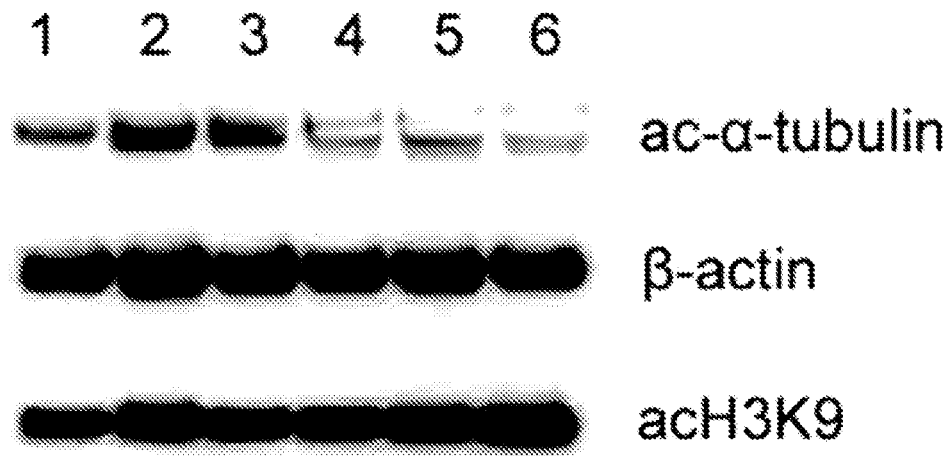
FIG. 3A shows Compound 2 induces tubulin hyperacetylation in rat dorsal root ganglion neurons (DRGN) as described in Example 6.

Dorsal root ganglion neurons (DRGNs) were treated with Compound 2 for 24 hours and whole cell extracts were analyzed by western blot. Compound 2 induced an increase in tubulin acetylation in a dose-dependent matter. Minimal histone acetylation increase is observed in DRGNs in response to Compound 2 at up to 1 uM. Compound 2 induces tubulin hyperacetylation in whole cell lysates of rat DRGNs (see FIG. 3A).

Figure 3B:
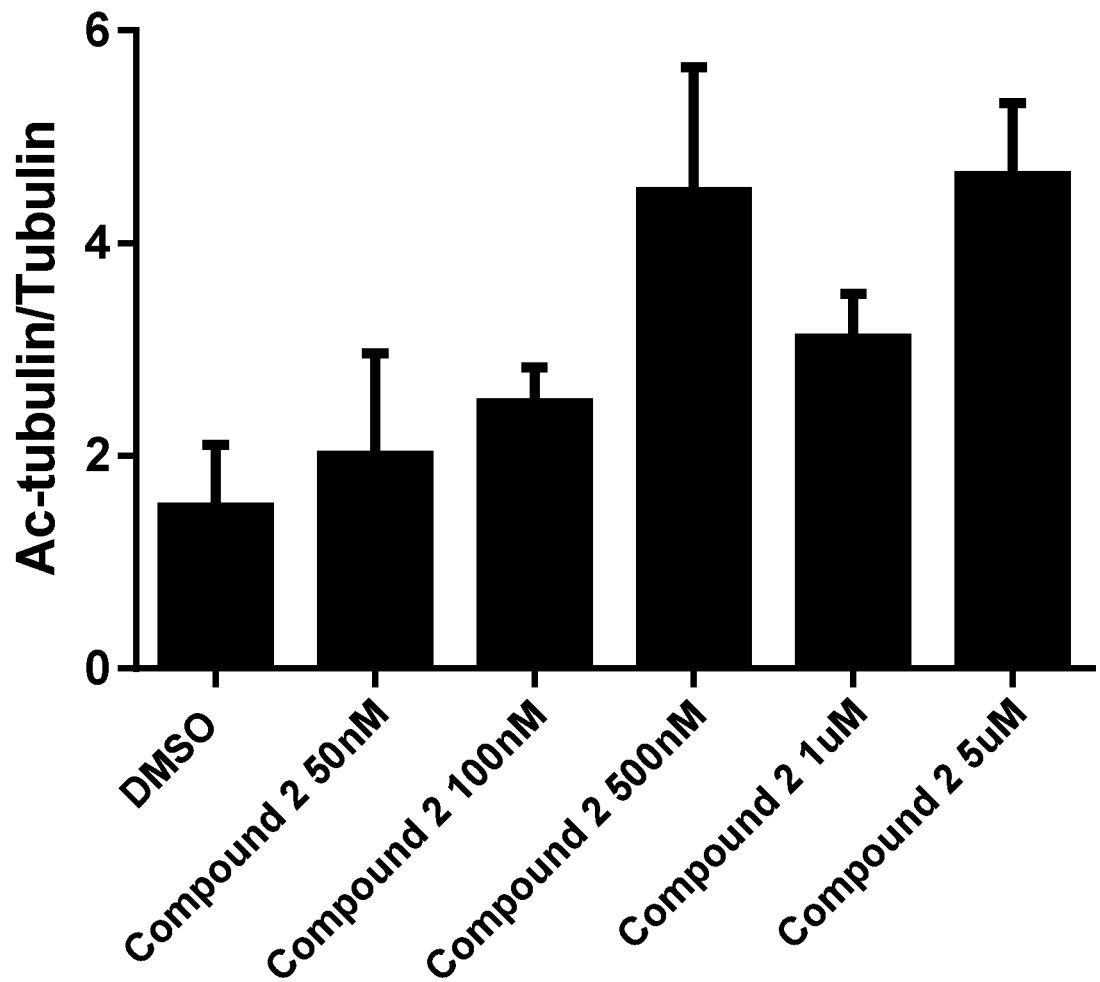
FIG. 3B shows Compound 2 increases acetylation of axonal microtubules as described in Example 6.

DRGNs were treated with Compound 2 on coverslips, fixed and stained with antibodies against acetyl-tubulin and total tubulin (fluorescent ICC) to visualize and quantitate tubulin acetylation in axonal microtubules. Compound 2 increases acetylation of axonal microtubules (See FIG. 3B). Acetyl-tubulin signal was normalized to total tubulin signal.

Example 7: HDAC6 Inhibitors do not Act as General Analgesics

A Tail Flick test was performed every hour in a time period of four hours after treatments. Rats were given Compound 1 or Compound 2 either for 4 days prior to the Tail Flick test (designated as BID groups) or in a single dose (QD groups) 1 h before the test.

Figure 4:
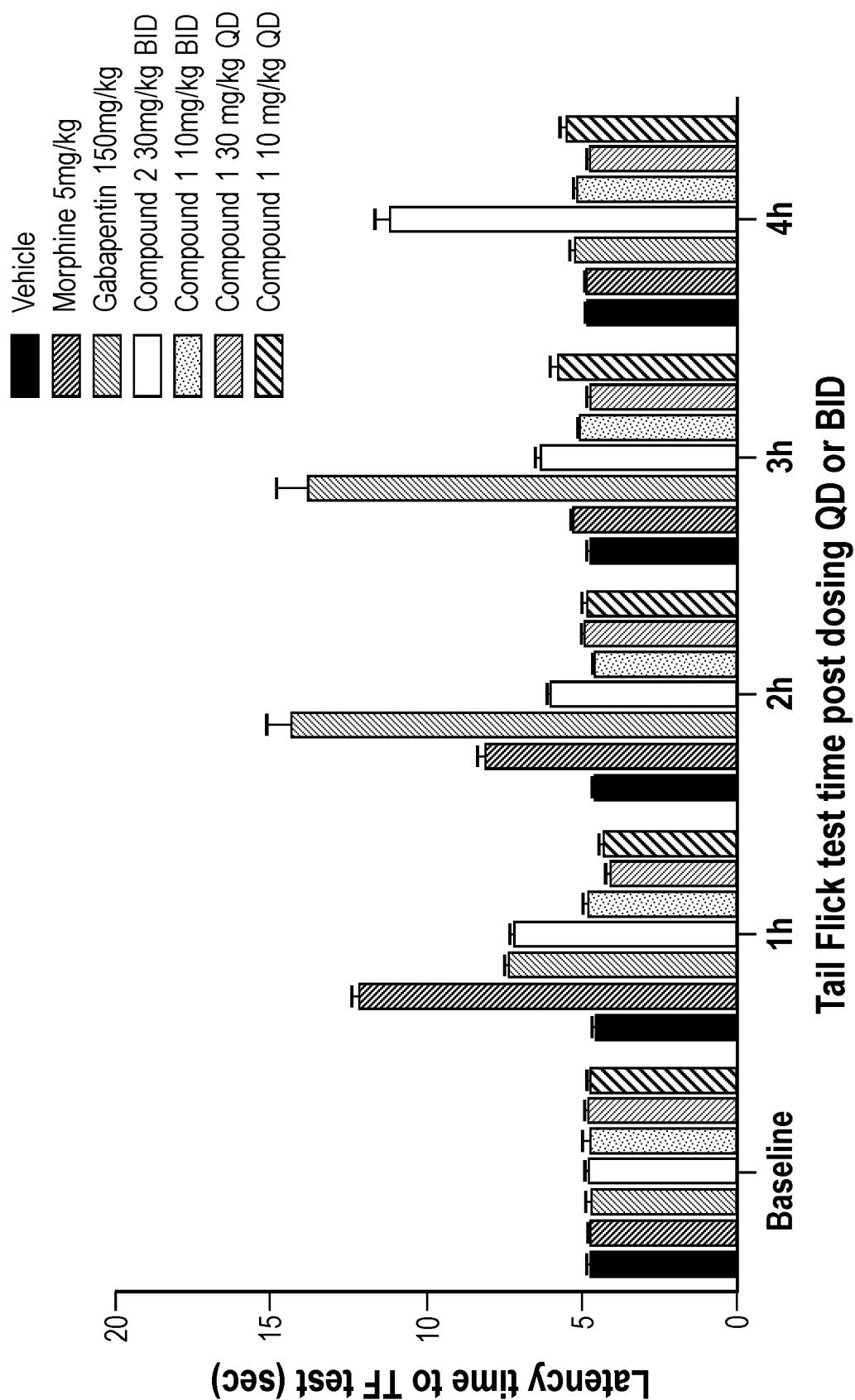
FIG. 4 shows the effects of Compound 1 and Compound 2 on latency time in the Tail Flick test described in Example 7.

Data are presented in FIG. 4 as the latency time in seconds until the animals flicked their tails in response to the heat source. Morphine and Gabapentin were used as positive controls. Treatments with Compound 1 and Compound 2 were not effective (except in the group that received Compound 2 at 30 mg/kg BID for 4 days) in increasing latency time when compared to vehicle control group Example 8: Metabolomic Study of HDAC6 Inhibitor Compound 1 in Diabetic Neuropathic Pain Model in Rats Metabolic stress underlies much of the pathology associated with diabetes. Freeman et al. (Freeman, O. J., Unwin, R. D., Dowsey, A. W., Begley, P., Ali, S., Hollywood, K. A., Rustogi, N., Petersen, R. S., Dunn, W. B., Cooper, G. J. S., Gardiner, N. J. (2016) "Metabolic Dysfunction is Restricted to the Sciatic Nerve in Experimental Diabetic Neuropathy" *Diabetes* 65) showed that in rats treated with streptozotocin to induce hyperglycemia, changes in metabolites in the sciatic nerve were associated with an increase in neuropathic pain.

Hyperglycemia was induced in rats with an injection of streptozotocin (60 mg/kg). Ten days later neuropathic pain was confirmed using a von Frey filament test for tactile allodynia. In this test, filaments of increasing diameter were applied to the plantar surface of the rear paw and the force necessary to precipitate a paw withdrawal is determined by the smallest filament needed to invoke a response. After tactile allodynia was confirmed the animals were dosed with Compound 1 twice per day at 10 mg/kg. At day 21 (11 days after the start of dosing) three each of vehicle and Compound 1 treated animals were sacrificed and the dorsal root ganglia and sciatic nerves were dissected from both sides and snap frozen. In addition, three naïve rats and three rats that had tactile allodynia at day 10 were sacrificed and the dorsal root ganglia and sciatic nerves were dissected and frozen as control samples.

Dorsal root ganglia and sciatic nerves were sent to Human Metabolome Technologies for analysis of metabolic intermediates. Extracts from these samples were analyzed by capillary electrophoresis/mass spectrometry to measure the level of charged metabolites. In addition, sciatic nerve extracts were analyzed by liquid chromatography/mass spectrometry to measure the level of non-charged metabolites.

Overall, 314 different metabolites were identified and 81 metabolites quantitated in sciatic nerve samples. 242 metabolites were identified and 83 quantitated in dorsal root ganglion samples. There were clear quantitative differences in metabolites in diabetic as compared to naïve rats in both tissues. As an example, the diabetic animals showed a large increase in sorbitol in the dorsal root ganglion tissues, which was reported in Freeman et al. (2016) for a similar animal model. In the sciatic nerve, diabetic animals showed a sharp decrease in the level of lysine, which was reported in Freeman et al. as well.

Figure 5A:
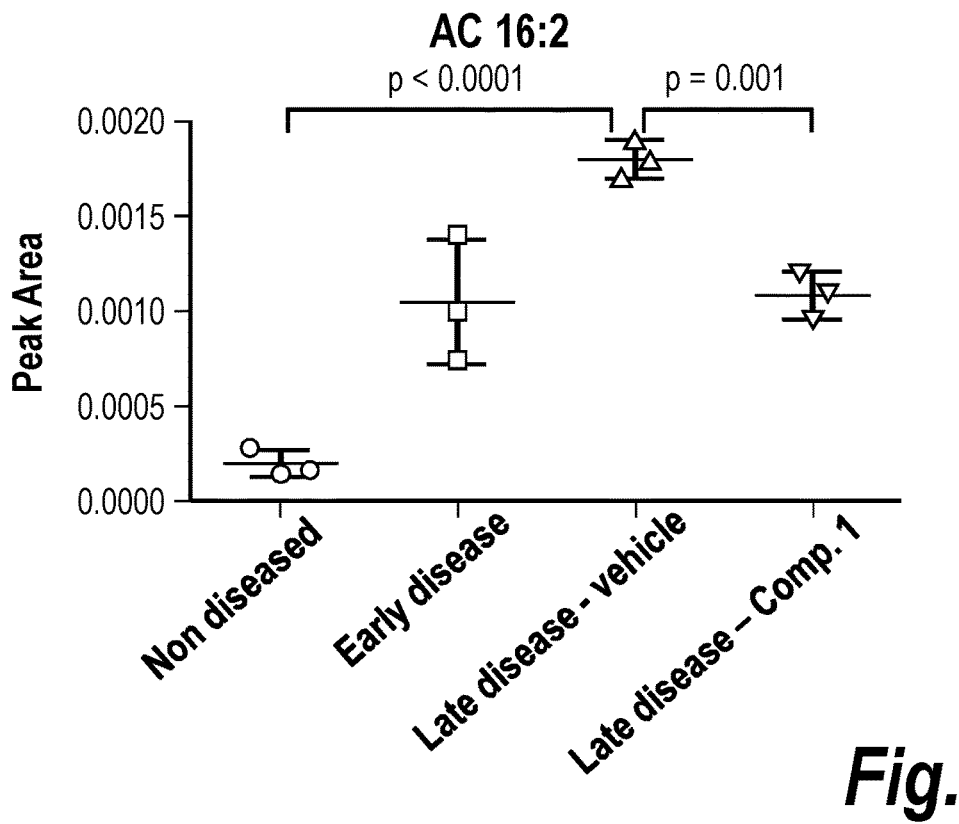
FIG. 5A shows changes in acyl-carnitines, AC 16:2 upon administration of vehicle or Compound 1 as described in Example 8.
Figure 5B:
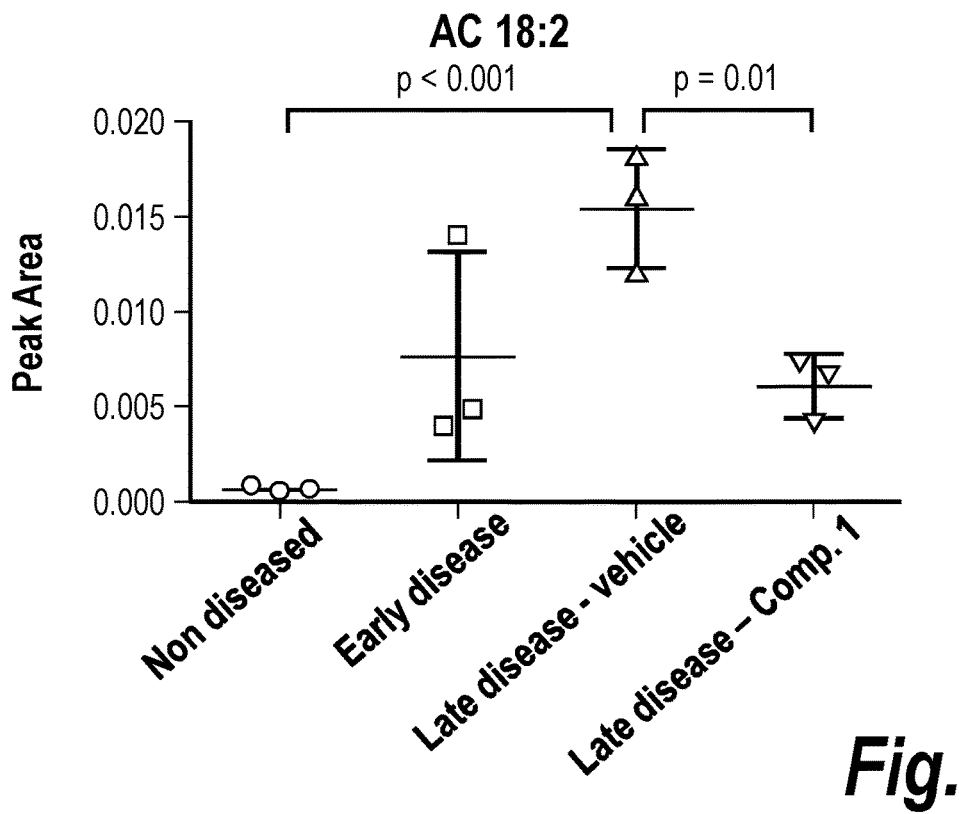
FIG. 5B shows changes in acyl-carnitines, AC 18:2 upon administration of vehicle or Compound 1 as described in Example 8.

The most dramatic changes in metabolites described in the Freeman paper occurred among the oxidized fatty acids, including acyl-carnitines. In our study the diabetic rats had a significant increase in several acyl-carnitines, including AC 16:2 (FIG. 5A) and AC 18:2 (FIG. 5B). Treatment with Compound 1 for 11 days normalized many of the metabolic changes, including the changes in acyl-carnitines. This reversal of acyl-carnitine buildup may represent one mechanism of neuroprotection by HDAC6 inhibition, since acyl-carnitine production in peripheral nerves is associated with axonal degeneration (Viader, A., Sasaki, Y., Kim, S., Strickland, A., Workman, C. S., Yang, K., Gross, R. W., Milbrandt, J. (2014) "Abberant Schwann Cell Lipid Metabolism Linked to Mitochondrial Deficits Leads to Axon Degeneration and Neuropathy" *Neuron* 77(5)).

In view of the Examples presented herein, HDAC6 inhibitors of Formulae Ia, I, and II, e.g., Compounds 1, 2, and 3 can be used for the treatment of DPN.

The invention claimed is:

1. A method for treating diabetic peripheral neuropathy in a subject in need thereof comprising administering to the subject a therapeutically effective amount of an HDAC6-specific inhibitor.

2. The method of claim 1, wherein the HDAC6-specific inhibitor is a compound of Formula II:

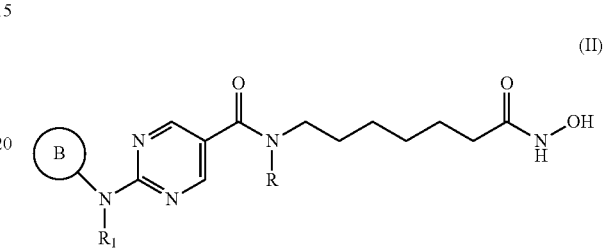

(II)

or a pharmaceutically acceptable salt thereof,
wherein ring B is aryl or heteroaryl optionally substituted by OH, halo, or $C_{1-6}$-alkyl;
$R_1$ is aryl or heteroaryl optionally substituted by OH, halo, or $C_{1-6}$-alkyl; and
R is H or $C_{1-6}$-alkyl.

3. The method of claim 2, wherein the compound of Formula II is:

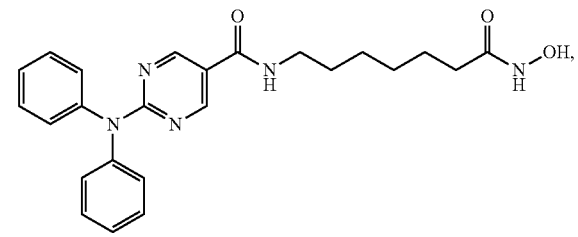 [SMILES: O=C(CCCCCCNC(=O)c1cnc(N(c2ccccc2)c2ccccc2)nc1)NO]

or a pharmaceutically acceptable salt thereof.

4. The method of claim 1, wherein the HDAC6-specific inhibitor is administered by oral administration.

* * * * *